US011285178B2

(12) United States Patent
Bain et al.

(10) Patent No.: US 11,285,178 B2
(45) Date of Patent: Mar. 29, 2022

(54) FERTILIZED EGG ISOLATE AND USES THEREOF

(71) Applicant: United Paragon Associates, Inc., Ottawa (CA)

(72) Inventors: Jerald Bain, Toronto (CA); Hao Chen, Columbia, MD (US); Joel Sadavoy, Toronto (CA); Arthur David Weissman, Baltimore, MD (US)

(73) Assignee: United Paragon Associates, Inc., Ontario (CA)

( * ) Notice: Subject to any disclaimer, the term of this patent is extended or adjusted under 35 U.S.C. 154(b) by 0 days.

(21) Appl. No.: 16/160,387

(22) Filed: Oct. 15, 2018

(65) Prior Publication Data

US 2019/0105355 A1   Apr. 11, 2019

Related U.S. Application Data

(63) Continuation of application No. 15/094,816, filed on Apr. 8, 2016, now abandoned, which is a continuation of application No. 12/812,355, filed as application No. PCT/CA2009/000019 on Jan. 9, 2009, now abandoned.

(60) Provisional application No. 61/033,184, filed on Mar. 3, 2008, provisional application No. 61/020,541, filed on Jan. 11, 2008.

(51) Int. Cl.
 *A61K 35/57* (2015.01)

(52) U.S. Cl.
 CPC .................... *A61K 35/57* (2013.01)

(58) Field of Classification Search
 CPC ............ A61K 35/57; A61P 9/10; A61P 43/00; A61P 29/00; A61P 25/28; A61P 25/24; A61P 25/22; A61P 25/18; A61P 25/08; A61P 25/00; A61P 21/02; A61P 15/10; A61P 15/00; A61P 13/10; A61P 13/02; A61P 11/00; A61P 1/04; A61P 1/00
 See application file for complete search history.

(56) References Cited

U.S. PATENT DOCUMENTS

| 5,641,517 | A  |   | 6/1997  | Eskeland et al.        |
|-----------|----|---|---------|------------------------|
| 2001/0033869 | A1 | * | 10/2001 | Eskeland ............ A61K 35/57 |
|           |    |   |         | 424/520                |
| 2011/0200737 | A1 |   | 8/2011  | Suyanto                |

FOREIGN PATENT DOCUMENTS

| JP | H08-502041 A | 3/1996 |
| JP | 2001302521 A | 10/2001 |
| WO | WO-94/03192 | 2/1994 |
| WO | WO-9403192 A1 * | 2/1994 ............. A61P 15/08 |
| WO | WO-98/22119 | 5/1998 |
| WO | WO-2007/047766 | 4/2007 |
| WO | WO-2007/108695 | 9/2007 |

OTHER PUBLICATIONS

Kovacs-Nolan et al. (2005) Journal of Agricultural and Food Chemistry 53(22): 8421-8431. (Year: 2005).*
Lyketsos et al. (1997) J. Neuropsych. Clin. Neurosci 9(4): 556-561 (Year: 1997).*
Kapczinski F. et al., Antidepressants for generalised anxiety disorder (GAD), 2003, Cochrane Database of Systematic Reviews, 2, 1-22 (Year: 2003).*
Gruenberg, A. et al. Classification of Depression: Research and Diagnostic Criteria: DSM-IV and ICD-10, 2005, Biology of Depression. From Insights to Therapeutic Strategies. Chapter 1, 1-12 (Year: 2005).*
Bilkei-Gorzo et al., "Diminished Axiety- and Depression-Related Behaviors in Mice with Selective Deletion of the Tac1 Gene," The Journal of Neuroscience, 22(22), pp. 10046-10052 (Nov. 15, 2002).
Cusin et. al., "Rating Scales for Depression," Handbook of Clinical Rating Scales and Assessment in Psychiatry and Mental Health, Hamana Press, Chapter 2, 30 pages (2010).
Decision of Refusal dated Mar. 22, 2016 in corresponding Japanese Patent Application No. 2014-162249 (3 pages).
International Search Report and Written Opinion dated Apr. 21, 2009 by the Canadian Intellectual Property Office as International Searching Authority for corresponding International Application No. PCT/CA2009/000019 (11 pages).
Maragos et al., "Glutamate dysfunction in Alzheimer's disease: an hypothesis," Trends in Neurosciences, 10, pp. 65-68 (Feb. 1987).
Nestler et al., "Neurobiology of Depression," Neuron, 34, pp. 13-25 ( Mar. 28, 2002).
OpioidRisk.com, "HAM-A" 2 pages, printed on Aug. 21, 2014, downloaded from <http://www.opioidrisk.com/node/1212>.
Second Office Action dated Dec. 26, 2012 in corresponding Chinese Patent Application No. 200980108589.4 (12 pages).
Supplementary European Search Report dated Nov. 22, 2011 in corresponding European Patent Application No. 09700397.4 (5 pages).
Written Opinion and Search Report dated Aug. 25, 2011 by the Hungarian Intellectual Property Office in corresponding Singaporean Patent Application No. 201004984-9 (16 pages).
Rosenthal, "Managing Depressive Symptoms in Substance Abuse Clients During Early Recovery: A Treatment Improvement Protocol—TIP 48", U.S. Department of Health and Human Services, Substance Abuse and Mental Health Services Administration, accessed at <https://www.ncbi.nlm.nih.gov/books/NBK64057/pdf/Bookshelf_NBK64057.pdf>, 2008 (174 pages).

* cited by examiner

*Primary Examiner* — Louise W Humphrey
*Assistant Examiner* — Anjali Ajit Hirani
(74) *Attorney, Agent, or Firm* — Wilmer Cutler Pickering Hale and Dorr LLP

(57) ABSTRACT

Fertilized egg isolate, methods for preparing the fertilized egg isolate and uses thereof for treating mental health disorders and disease or conditions mediated by or associated with one or more glutamate receptors or by the neurokinin 2 (NK2) receptor.

9 Claims, 12 Drawing Sheets

| ANALYSIS | SPECIFICATION | ACTUAL RESULTS |
|---|---|---|
| Protein | Minimum 60% | 73% |
| Fat | Minimum 10% | 13% |
| Ash | Maximum 6% | 4% |
| Moisture | Maximum 5% | <2% |
| Purity (HPLC, on protein) | ≥90% | ≥90% |
| Standard Plate Count | $<1\times10^5$ CFU/gram | $<1\times10^5$ CFU/gram |
| Yeast & Mold | $<1\times10^3$ CFU/gram | $<1\times10^3$ CFU/gram |
| *Salmonella spp.* | $<1\times10^1$ CFU/gram | $<1\times10^1$ CFU/gram |
| *E. Coli* | $<1\times10^1$ CFU/gram | $<1\times10^1$ CFU/gram |
| *S. aureus* | $<1\times10^1$ CFU/gram | $<1\times10^1$ CFU/gram |

Figure 7

FERTILIZED EGG ISOLATE AND USES THEREOF

CROSS-REFERENCE TO RELATED APPLICATIONS

This is a continuation of U.S. application Ser. No. 15/094,816, filed Apr. 8, 2016 which is a continuation of U.S. application Ser. No. 12/812,355, filed Sep. 21, 2010, which is a National Stage Entry of PCT/CA09/00019, filed Jan. 9, 2009, which claims the benefit of U.S. Provisional Application No. 61/020,541, filed Jan. 11, 2008 and U.S. Provisional Application No. 61/033,184, filed Mar. 3, 2008, which are hereby incorporated by reference.

FIELD OF THE INVENTION

The invention relates to fertilized egg isolate including that prepared by any of the processes set forth in the description and uses thereof for treating mental health disorders.

BACKGROUND OF THE INVENTION

Major depressive disorder (also known as major depression, clinical depression, unipolar depression and unipolar disorder) is very prevalent in the general population. Most recent North American data show a 14.5% lifetime risk of major depression in adults and 8.1% one year prevalence (Results from the 2004 National Survey on Drug Use and Health: National findings; Revisions as of Sep. 8, 2005; Department of Health and Human Services. Substance Abuse and Mental Health Services Administration Office of Applied Studies).

The mean duration of a depressive episode with modern treatments is about 16 weeks, although some data suggest a longer duration of about 6-8 months, far less than in the pre-antidepressant therapy era when the duration was about 18 months (Kendler, McLeod, Patten).

Antidepressants have had a very positive impact on the treatment of depression and on reducing the suffering of patients. Patients with depression are often impaired in function and frequently have co-morbid disorders such as substance abuse that can be attributed to the underlying depression. Depression leads to increased utilization of health services and can have a devastating impact on social structure and societal economics.

The cause of depression is not fully known. Disturbance of monoamine synthesis and activity has been a prominent etiological theory of depression for the past few decades and support for this has been strengthened by the effectiveness of medications that enhance monoamine activity, particularly those which are serotonergic and/or noradrenergic. However, any given antidepressant is only effective in a subset of depressed patients and often only partially so. Current treatments administered in controlled trials in academic settings with selected samples show efficacy in only about 60% of patients and only about half of these have full remission of symptoms. This is important since the presence of residual symptoms is a strong predictor of relapse. There are other physiological changes associated with depression which suggest a more complex interplay of etiological factors including the role of second messengers mediating membrane bound and intracellular processes. This has led to investigation of hormonal pathways such as the hypothalmic-pituitary-adrenal (HPA) axis (the activity of which is elevated in 20-40% of community-dwelling patients with depression), thyroid axis (5-10% of patients evaluated with depression have previously undetected thyroid dysfunction), growth hormone, prolactin and the role of inflammatory processes and their markers such as interleukin 1 and 6 and tumour necrosis factor.

Most persons with major depressive disorder experience some degree of symptom return, and 20-30% exhibit a chronic course (defined as a syndromal level of depressive symptom severity for two years or more (Treatment of Chronic Depression (Editorial))).

All depressed persons require continuation of pharmacotherapy to prevent relapse and permit recovery. A substantial proportion of depressed patients require maintenance pharmacotherapy to prevent recurrence and further consolidate psychosocial recovery. However, while one of the major factors in effective antidepressant therapy is maintaining the patient on an adequate dose of medication for an adequate duration, this is often difficult. Many patients fear taking current antidepressants because of real or imagined physical effects. Some patients prefer to use so-called natural health promoting substances and non-pharmacological interventions. Patients who are prepared to take antidepressants often encounter a wide array of side effects which leads them to be non-compliant or to reject therapy entirely. Selective serotonin reuptake inhibitors (SSRI) for example, commonly induce gastrointestinal upset, headaches, sleep disturbance and significant sexual impairments among many other side effects. Most antidepressants have at least some significant side effects and these limit clinicians' capacity to effectively treat many patients.

Depression can be associated with other disorders and/or syndromes, including anxiety, such as generalized anxiety disorder, sexual dysfunction, seasonal affective disorder, social anxiety disorder, otherwise known as social phobia, bipolar disorder, and dementia.

It is widely acknowledged that the limited efficacy, often unacceptable side effects and physiological factors that may induce or otherwise affect the course of depression make it necessary to continue to search for new compounds with novel pharmacological actions to address the major public health problem of depression.

BRIEF DESCRIPTION OF THE FIGURES

The person skilled in the relevant arts will understand that the figures, described below, are for illustration purposes only. The figures are not intended to limit the scope of the invention in any way.

FIG. 7 shows the results of analyses of a fertilized egg isolate according to embodiments of the present invention.

DETAILED DESCRIPTION OF THE INVENTION

Figure 1:
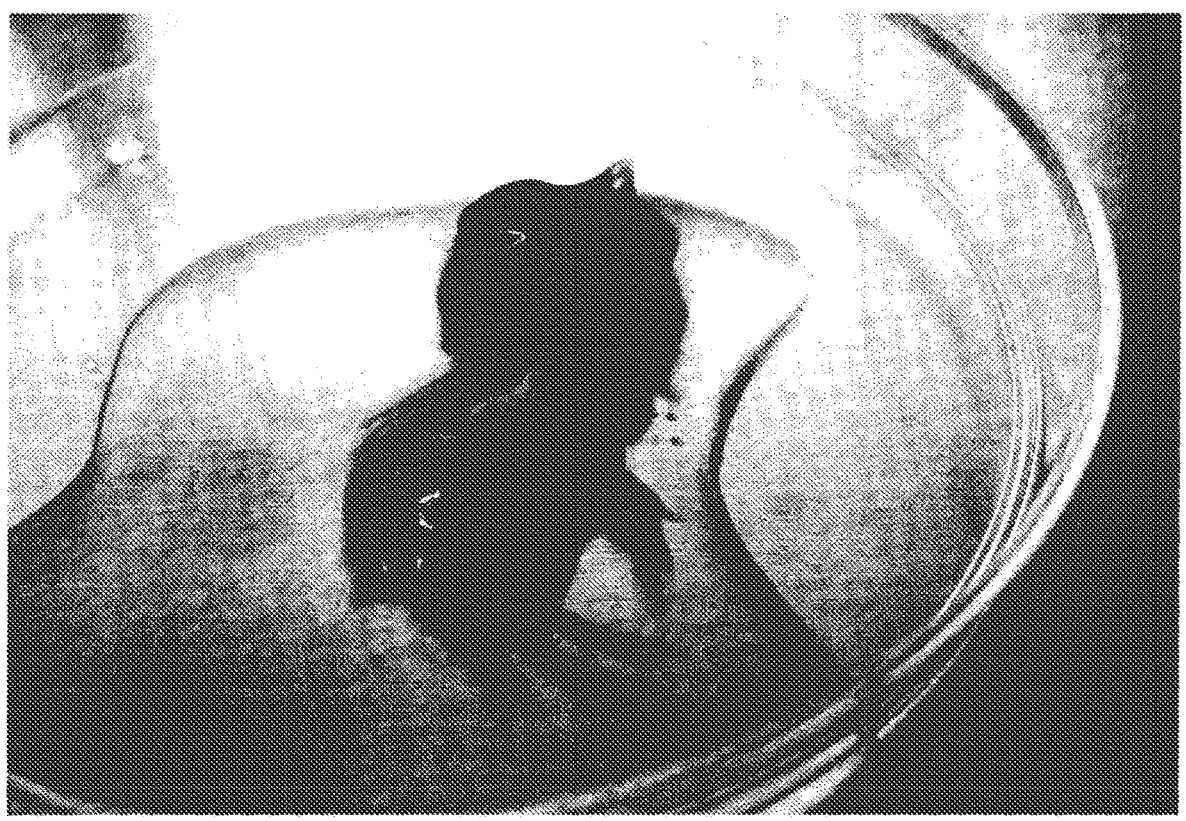
FIG. 1 is an image of an embryo removed from an egg according to embodiments of the present invention.

In accordance with the present invention, fertilized egg isolates and uses thereof to treat mental health disorders are described.

Fertilized Egg Isolates—Preparation

In accordance with an aspect of the invention, a process for preparing a powdered sample of at least one embryo or preparing a powdered sample from a portion or all of the contents of a fertilized egg is provided. At least one fertilized egg is incubated for anywhere from about 3 to about 15 days, more preferably about 3 to about 5 days, or more preferably about 6 to about 12 days, and even more preferably about 7 to about 9 days, from the day the egg is fertilized. Generally speaking, the fertilized egg is incubated for a period of time that allows angiogenesis to initiate and/or the embryo to mature to the point that embryos are visible to the naked eye. The eggs can be from a variety of origins, for example, avian, reptilian, or from egg-laying mammals. Generally speaking, any egg from which an embryo or blood vessels associated with an embryo can be removed can be suitable. The eggs are preferably avian eggs, and can be obtained from any bird that has been bred for egg production, such as chicken, geese, ducks, and the like. Chicken eggs are preferred for reasons including their availability and ability to be mass produced. Incubation can occur in any environment, so long as the eggs are kept at a temperature for extended periods of time that allows maturation of the embryo. Suitable temperatures for incubation are in the range of about 20° C. to about 60° C., more preferably in the range of about 25° C. to about 55° C., and more preferably in the range of about 35° C. to about 45° C. Once the eggs are incubated for a period of time, they are optionally treated to reduce external microflora or otherwise sterilized by any suitable means, such as washing the egg shells with a solvent such as ethanol, for example, an about 50% to about 95% solution of ethanol, with subsequent time allowed to allow evaporation or drying of the solvent, or by rotating the eggs under an ultraviolet (UV) light source for a suitable period of time. Any solvent is preferably evaporated before further manipulation of the egg. The eggs are then cracked to access the inner contents. The eggs can be cracked under aseptic conditions either manually or using a suitable mechanical device. This procedure and/or all or most of the procedures described above and below can be conducted in a cooled atmosphere, such as an atmosphere of about 5° C.

According to one aspect of the invention, the contents of the egg are collected in a container, such as a stainless steel container, which is preferably sterilized and/or chilled. The contents from the container or from the egg can optionally be subjected to a filtration process, for example, by being placed on a mesh. The mesh openings can be about 0.5 to about 4 millimeter, more preferably about 1 millimeter. The mesh is preferably sterile.

Optionally, the contents of the egg and/or some or all of the broken shell can be placed directly on the mesh. The contents of the egg and/or some or all of the broken shell are allowed to filter on the mesh for a period of time such that there is substantially no further dripping of fluid through the mesh. The broken shell can be removed from the contents of the egg before, during, or after the filtration process. After the filtration, the solid or solid and semi-solid retentate can comprise the embryo, vascular connective tissue, a substantial portion or all of the albumen, a substantial portion or all of the chalaza, and the clear sac. Semi-solid retentate can comprise solid material as well as a viscous material, such as a gelatinous material, for example, albumen. The retentate or semi-solid retentate can be optionally washed at least once with a suitable solvent, such as a buffer solution, sterile deionized water, or any suitable saline solution. For example, sterile phosphate buffer saline (PBS) can be used.

The retentate can be collected from one egg and then freeze-dried according to the processes described herein, or the retentate can be collected from one or more eggs together, and then freeze-dried according to the processes described herein.

According to another aspect of the invention, the white albumen portion and/or embryo can be substantially separated from the rest of the contents of the egg. The white albumen portion may be substantially separated from the rest of the contents by any suitable means, such as decantation of the white albumen portion, or by suction. The embryo can be substantially separated from the white albumen portion manually or other suitable means as determined by the skilled person. FIG. 1 shows an example of an embryo that was removed from an egg and washed with buffer. It will be recognized by those skilled in the art that the embryo can be substantially separated from the white albumen portion and the rest of the inner contents at the same time. For example, the embryo can be manually removed from the white albumen portion and rest of the inner contents using tweezers or other suitable instrument. In some cases, the embryo can be manually peeled off the yolk sac, which forms part of the rest of the inner contents.

Once the embryo is substantially separated from the white albumen portion and the rest of the inner contents of the egg, the embryo is optionally washed at least once with a suitable solvent, such as a buffer solution, sterile deionized water, or any suitable saline solution. For example, sterile phosphate buffer saline (PBS) can be used.

It will be understood for the following methods that reference to contents of the egg may actually be a reference to the retentate if the contents have been subjected to a filtration process. It will also be understood that a whole fertilized egg can be cracked, the shell removed, and the whole of the shelled egg frozen and freeze-dried according to any of the procedures described above and below, to produce a fertilized egg isolate of the present invention. Also, more than one whole fertilized egg can be cracked, shells removed, the whole of the shelled fertilized eggs combined and blended into a slurry, and frozen and freeze-dried according to any of the procedures described above and below.

Figure 2:
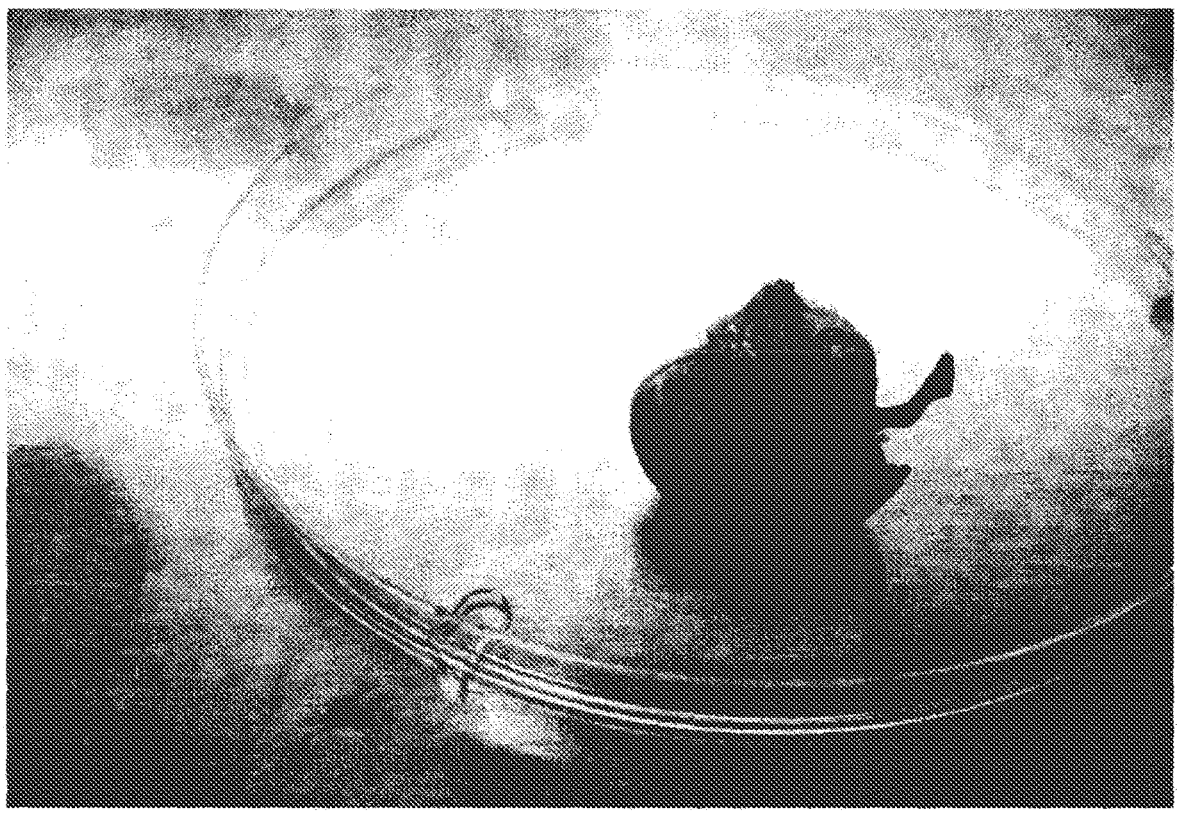
FIG. 2 is an image of a freeze-dried embryo according to embodiments of the present invention.
Figure 3:
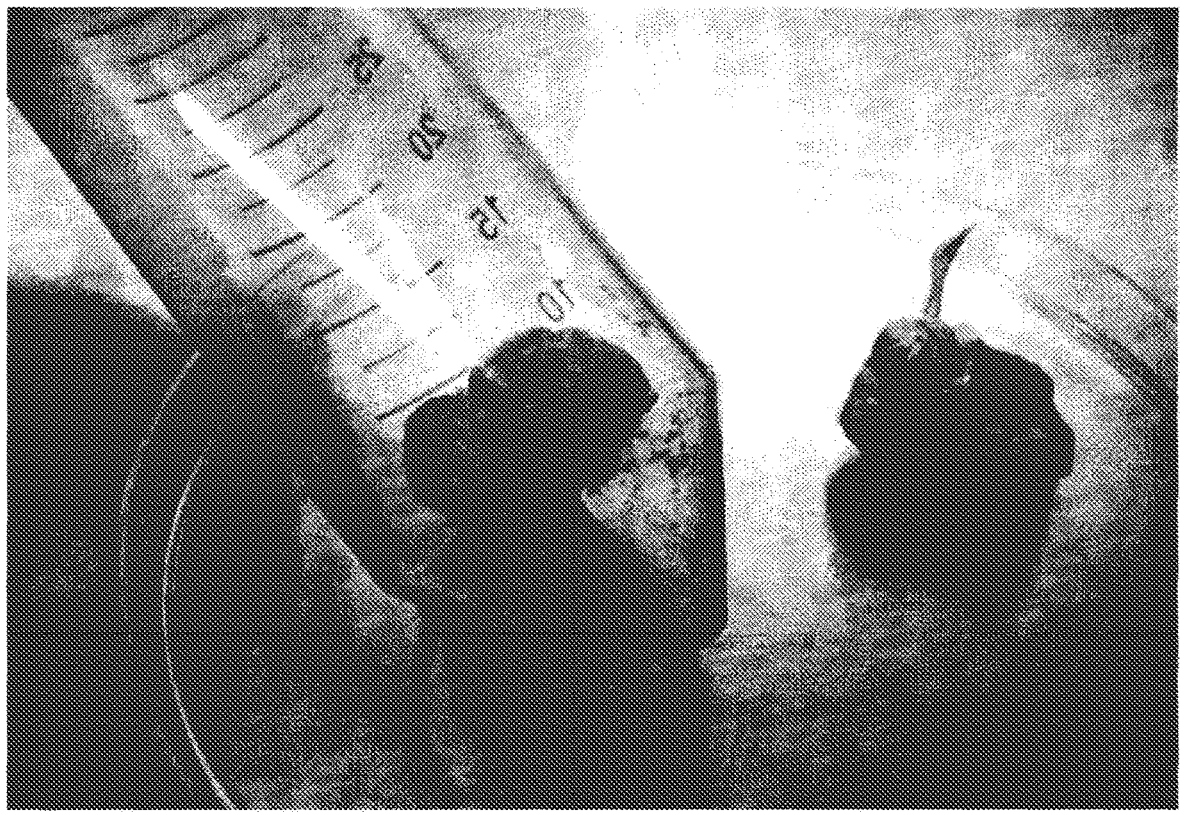
FIG. 3 is an image of freeze-dried embryos according to embodiments of the present invention.

The contents of the eggs or the embryos are placed in at least one freezable container. The container can be, for example, a test tube, Petri dish, beaker, stainless steel tray, or plastic container. It is preferred that the contents or embryos are frozen very soon after being removed from the shell, such as within about 2 hours, more preferably within about 1 hour, and even more preferably within about 0.5 hours, or as soon as possible. Depending on how long the contents or embryos are to be frozen, the freezing temperature should be in the range of about −50° C. to about 10° C., more preferably in the range of about −40° C. to about 5° C., and even more preferably in the range of about −35° C. to about −25° C. It is preferred that the contents or embryos are frozen for at least about 6 hours, more preferably at least about 12 hours, even more preferably at least about 24 hours. The frozen contents or embryos may be freeze-dried or lyophilized after a period of time. The contents or embryos can be completely frozen before the freeze-drying/lyophilizing step. FIGS. 2 and 3 show examples of embryos after they have been freeze-dried.

Optionally, frozen or unfrozen contents or embryos can be pooled in a suitable container, such as a beaker, or a plastic container, and mixed or blended with a suitable solvent, if necessary, to form a slurry. The solvent can be suitably aqueous to wet the mixed contents or embryos and be able to be frozen in a standard laboratory freezer. Suitable solvents include water, aqueous buffer, and the like. To form the slurry, it is preferred that the contents and/or embryos are blended. The contents or embryos can be blended or homogenized with, for example, a hand-held blender or other suitable means. The slurry can then be frozen as described above and freeze-dried. Freeze-drying is preferably performed at an ultimate temperature in the range of about −80° C. to about −10° C., more preferably in the range of about −65° C. to about −15° C., and even more preferably in the range of about −40° C. to about −20° C. and a pressure of about 500 millitorr, or other suitable pressure as can be determined by the skilled person. The freeze-drying process is preferably maintained at the ultimate temperature for a period of in the range of about 1 to about 6 hours, more preferably in the range of about 2 to about 5 hours, and even more preferably in the range of about 3 to about 4 hours. The whole freeze-drying process is typically conducted for a period in the range of about 15 to about 45 hours, more typically in the range of about 25 to about 35 hours, and even more typically in the range of about 28 to about 32 hours.

Figure 4:
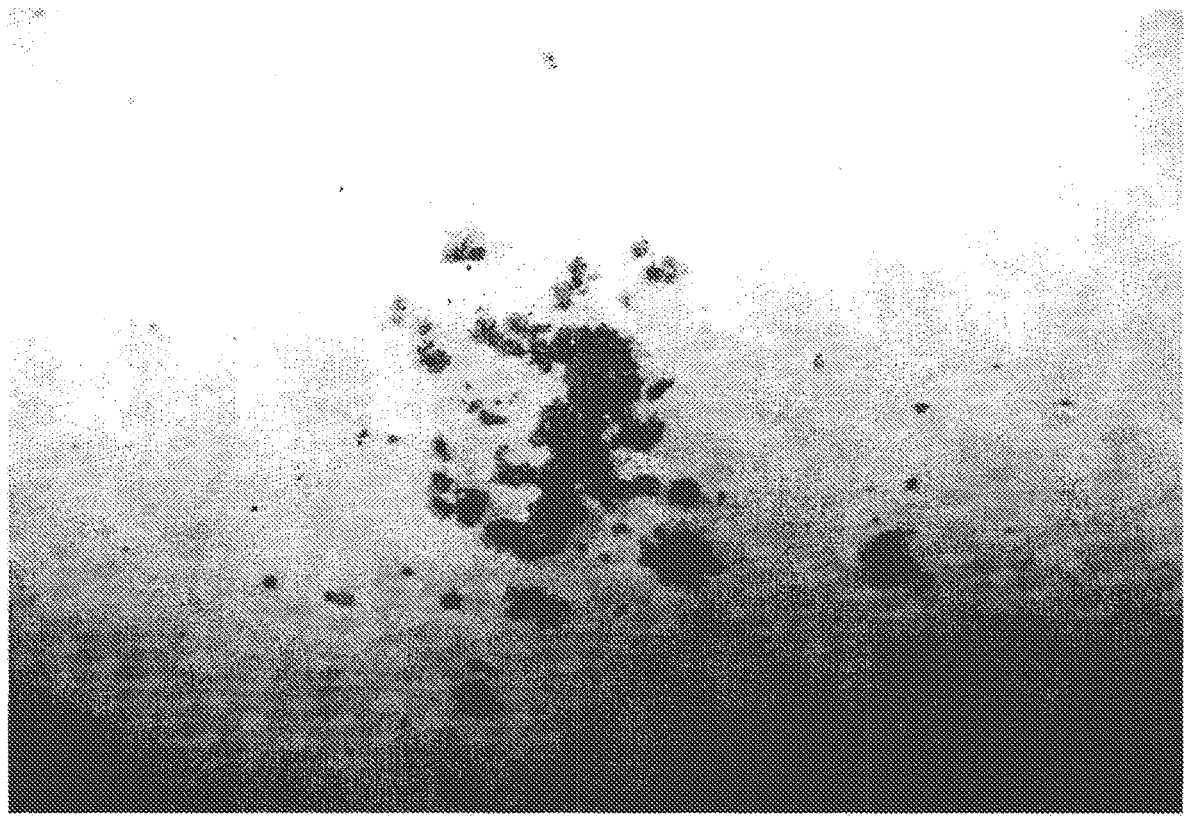
FIG. 4 is an image of pulverized freeze-dried embryo according to embodiments of the present invention.

In accordance with another aspect of the invention, the freeze-dried contents, freeze-dried embryo, or freeze-dried slurry is dispersed and/or pulverized if necessary to form a substantially homogeneous powder. The contents that were freeze-dried individually or in smaller groups can be combined together before or after the pulverization step to form a substantially homogeneous powder. The pulverization can be done, for example, mechanically using a suitable machine, such as a coffee bean grinder or a hammer mill, or manually using a suitable tool, such as a glass rod. FIG. 4 shows an example of pulverized freeze-dried embryo. The powder is optionally sterilized before being stored and/or used. A suitable sterilization should be one that does not adversely affect certain freeze-dried components.

In association with any process described herein, preservatives to control microbial growth can be blended into the powder or concentrate before it is stored. Preservatives can also be added at another stage of the manufacture, including before the freeze-drying or concentration step instead of, or in addition to, being added to the powder or concentrate. Suitable preservatives include common food preservatives such as 0.5% w/w sodium benzoate and 0.2% w/w potassium sorbate. Other suitable preservatives could be selected by the skilled person.

The powders produced by the processes disclosed herein can be stored in suitable, substantially air-tight containers. Suitable containers include plastic bags, barrels, plastic containers, bottles, combinations thereof, and the like. For example, the powder can be packaged under controlled, aseptic conditions into sterile polyethylene/polypropylene bottles with tamper-proof security seals. The powder can be stored under a substantially dry, inert gas, such as nitrogen. It is preferred that the powder be stored at room temperature or cooler, for example, at a temperature in the range of about 10° C. to about 25° C., more preferably in the range of about 15° C. to about −20° C. For long term storage, it is preferred that the powder is stored at a temperature of about −10° C. or below, or, more preferably, −20° C. or below. The powder can be stored for a period of time in a substantially desiccated atmosphere. The powder can also be vacuum-packed.

Figure 5:
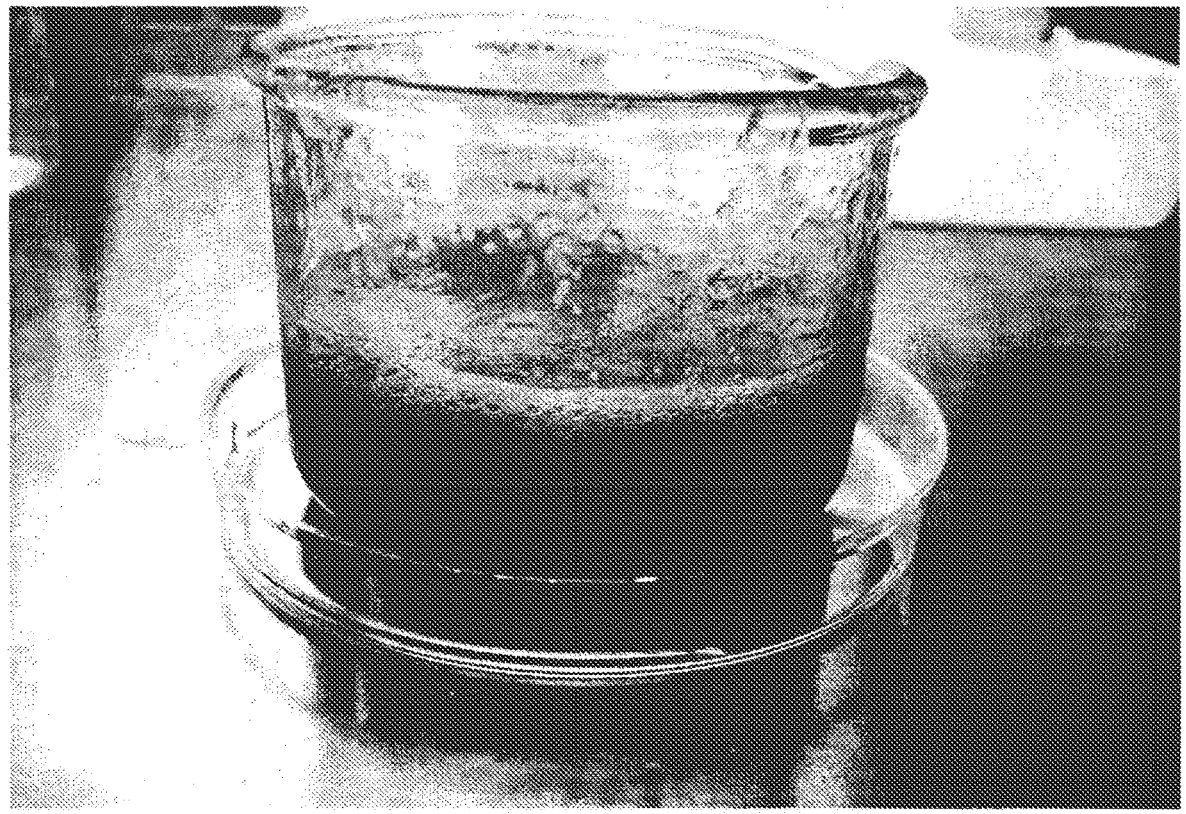
FIG. 5 is an image of a slurry of a number of embryos according to embodiments of the present invention.

In accordance with another embodiment of the present invention, a slurry is prepared as described above, or can be prepared by separating the contents or embryos of at least one fertilized egg from the egg shell, and pooling the separated contents or embryos in a suitable container. The separated contents or embryos can be cooled during this step. For example, the container can be placed on ice to facilitate cooling. The contents or embryos can be blended by methods described above to produce a slurry. FIG. 5 shows an example of a container of a slurry of embryos. The slurry can be freeze-dried as described above, or partially or wholly used for extraction procedures as follows.

An aqueous extraction procedure can be performed by mixing the slurry with an aqueous solution for a period of time. The aqueous solution may comprise water, an aqueous buffer, or any other aqueous solvent. If the aqueous solution comprises water, it is preferred that the water is distilled and, more preferably, also deionized before use. For example, the water can be treated using reverse osmosis (R.O.). The slurry and the aqueous solution can be mixed, for example, by stirring for a period of time, the period of time being in the range of about 5 to about 60 minutes, more preferably in the range of about 10 to about 45 minutes, and even more preferably in the range of about 15 to about 40 minutes. It is desired that the aqueous solution has sufficient exposure to the contents of the slurry so that any substantially hydrophilic molecules in the solution are dissolved in the aqueous solution. The aqueous solution can be of a substantially equal volume to the slurry, but volumes of 1.5 times, 2 times, or even 3 times the volume of the slurry can be used. Optionally, the mixture can be warmed slightly during the mixing step. After the mixing, the aqueous solution can be substantially clarified by substantially removing any solid portions in the mixture by suitable means such as centrifugation or filtration. The clarified aqueous portion can then be frozen and freeze dried to produce a powder that is optionally sterilized according to methods described herein.

According to another aspect of the invention, the slurry produced by any of the methods described above can be mixed with a substantially hydrophobic solvent. The substantially hydrophobic solvent is preferably chilled. Suitable hydrophobic solvents include, for example, ether, chloroform, hexane, petroleum ether, or acetonitrile. For example, ether, especially diethyl ether, can be used. The slurry is mixed with the hydrophobic solvent for a period of time as described above. As will be recognized by a person skilled in the relevant arts, any steps of a process using a substantially hydrophobic solvent should be conducted in a fume hood or similar device, and the solvents should be kept away from open flames or heat sources. After the mixing period, the solid portions of the mixture can be substantially removed from the solvent portion by suitable means such as centrifugation or filtration. The solvent portion will comprise substantially a hydrophobic solvent portion and may also comprise an aqueous portion. The solvent portion can be transferred to a separating funnel or essentially equivalent device to separate the aqueous portion from the hydrophobic solvent portion. If the top layer is the hydrophobic solvent portion, it can be siphoned off the top or removed from the separating funnel after the bottom aqueous layer is removed. Alternatively, the bottom aqueous portion can be frozen, thereby allowing the top ether-based layer to be decanted. The aqueous portion can be extracted a number of times, for example, about 3 times, with the hydrophobic solvent. The hydrophobic solvent can be of substantially equal volume to the aqueous portion, or can be 1.5 times, 2 times or even 3 times the volume of the aqueous solvent. Other ratios may also be suitable.

After the extraction process, all of the hydrophobic isolates can be pooled and concentrated by a suitable method. The concentrated isolates can be stored at a temperature below room temperature, such as about 5° C. in a suitable container that is substantially sealed from the atmosphere, such as a sealed vial.

According to another aspect of the invention, a slurry produced by any of the methods described above can be clarified before an extraction procedure. Preferred clarification steps include methods of filtration, using such filters as sieves or filter papers or pads. Other clarification steps can include methods of centrifugation. A filter aid, such as Superflow DE™ can be added to the filtrate produced by the filtering step before further clarification. Some of the resultant filtrate can be frozen in suitable containers for freeze-drying. Also, some of the resultant filtrate can be mixed with a hydrophobic solvent as described above so that an aqueous layer and a hydrophobic layer are formed. The layers can be separated, concentrated, and stored as described herein.

The fertilized egg isolate prepared by various processes described herein could be formulated to increase potency by repeating and/or combining processes. For example, aqueous and/or hydrophobic solvent extraction can be repeated on the same sample to concentrate active compounds.

Fertilized Egg Isolate—Uses

Fertilized egg isolate as prepared by the processes described herein, or as prepared by similar processes which will be readily apparent to the skilled person upon learning of the present invention, can be used to treat patients suffering from mental health disorders, including depressive mood disorders, such as major depressive disorder, dysthymic disorder, depressive phase of bipolar disorder, depression due to a general medical condition such as depression associated with dementia or schizoaffective disorder, substance-induced depression and seasonal affective disorder, anxiety disorders, such as generalized anxiety disorder, social phobia and panic disorder, and sexual dysfunction. As will be appreciated by those skilled in the relevant arts, treating such disorders as depression or anxiety can be a useful approach for treating other disorders and/or syndromes with which they may be associated, such as those listed above. In one embodiment, the patient is a human.

As described in detail herein, it has been determined that the fertilized egg isolate of the present invention antagonizes the binding interactions of certain ligands with their receptors. In particular, it has been found that the fertilized egg isolate of the present invention has the capacity to displace glutamate from four of its major receptors. In addition, the fertilized egg isolate can displace the neurotransmitter neurokinin A (NKA) from its receptor, neurokinin 2 (NK2 receptor). To the knowledge of the present inventors, this is the first known instance in which these two receptor groups have been shown to be antagonized by a single substance.

Glutamic acid (glutamate) is one of the most excitatory substances within the human brain. A number of diseases and conditions are known to be mediated by or associated with activation of one or more glutamate receptors. These diseases and conditions include depression (see, for example, Paul, Toro, Mathew 2005, Krystal, Sanacora 2003, Svenningsson, McNally), major depressive disorder (see, for example, Maeng, Chourbaji, Mathew 2008), anxiety (see, for example, Rorick-Kehn), Alzheimer's disease (see, for example, Walton, Koch, Hynd), epilepsy (see for example, Kew, Vincent), schizophrenia (see, for example, McCullumsmith, Lewis, MacDonald, Javitt), impairment of brain cell function after stroke/ischemia (see, for example, Ginsberg, Kew), amyotrophic lateral sclerosis (Lou Gehrig's Disease) (see, for example, Mathew 2008, Miller), lathyrism (see, for example, Spencer, Ravindranath), autism (see, for example, Chez), mental retardation (see, for example, Bowie), disturbances of cognition (see, for example, Cheon), bipolar depression (see, for example, Mathew 2008) and mania (see, for example, Krystal). Furthermore, it has been shown that antagonists of the glutamate receptor, such as ketamine and riluzole can be used to treat depression (Mathew 2008), major depressive disorder (Maeng, Mathew 2008, Zarate 2004, Sanacora 2007), amyotrophic lateral sclerosis (Mathew 2008, Miller) and bipolar depression (Mathew 2008, Zarate 2005). The inhibition of activation of one or more glutamate receptors, by inhibiting glutamate's binding to its receptor, can diminish or eliminate conditions or diseases mediated by or associated with one or more glutamate receptors. Since it has been determined, as described herein, that the fertilized egg isolate of the present invention binds to one or more glutamate receptors, the fertilized egg isolate of the preset invention can be used to treat diseases and conditions associated with or mediated by one or more glutamate receptors.

Accordingly, another aspect of the invention features a method for treating a disease or condition associated with or mediated by a glutamate receptor using fertilized egg isolate, the method comprising the step of administering a therapeutically effective amount of the fertilized egg isolate to a patient in need thereof. Among such glutamate receptors are the ionotropic glutamate receptors, for example, the α-amino-3-hydroxyl-5-methyl-4-isoxazole-propionate (AMPA) receptor, the kainate receptor and the N-methyl-D-aspartic acid (NMDA) receptor. The disease or condition associated with or mediated by a glutamate receptor can include depression, major depressive disorder, anxiety, Alzheimer's disease, epilepsy, schizophrenia, impairment of brain cell function after stroke/ischemia, amyotrophic lateral sclerosis (Lou Gehrig's Disease), lathyrism, autism, mental retardation, disturbances of cognition, bipolar depression or mania.

A number of diseases and conditions are also known to be mediated through or associated with activation of the NK2 receptor. Such diseases or conditions include depression (see, for example, Dableh, Ahlstedt, Michale, Louis, Steinberg, Salomé, Holmes, Steinberg, Husum), anxiety (see, for example, Ahlstedt, Michale, Louis, Greibel, Steinberg, Stratton, Teixeira, Walsh, Salomé, Holmes), irritable and inflammatory bowel syndrome (see, for example, Ahlstedt, Lecci, Evangelista, Toulouse), inflammatory airway diseases (see, for example, Bai) and urinary incontinence (see, for example, Ahlstedt, Rizzo). Furthermore, it has been shown that antagonists of the NK2 receptor, such as saredutant (SR 48964) can be used to promote antidepressant-like effects (Salomé, Dableh, Steinberg, Michale, Louis) and anxiolytic effects (Teixeira, Salomé, Griebel, Michale, Louis) in animal models, and studies in humans have also been conducted. The inhibition of activation of the NK2 receptor, by inhibiting NK2's endogenous ligand(s), e.g., NKA from binding to its receptor, can diminish or eliminate conditions or diseases mediated by or associated with the NK2 receptor. Since it has been determined, as described herein, that the fertilized egg isolate of the present invention binds to the NK2 receptor, the fertilized egg isolate of the present invention can be used to treat diseases and conditions associated with or mediated by the NK2 receptor.

Accordingly, another aspect of the invention features a method for treating a disease or condition associated with or mediated by an NK2 receptor using fertilized egg isolate, the method comprising the step of administering a therapeutically effective amount of the fertilized egg isolate to a patient in need thereof. The diseases or conditions associated with or mediated by an NK2 receptor can include depression, anxiety, irritable bowel syndrome or urinary incontinence.

The fertilized egg isolate used in the treatment of a disease or condition associated with or mediated by one or more of a glutamate receptor and an NK2 receptor can comprise freeze-dried embryo, ovalbumin, and clear sac from the fertilized egg or it can be produced such that it does not comprise a substantial amount of the yolk from the fertilized egg. The fertilized egg isolate can be prepared according to methods described herein, or by similar methods known to those skilled in the art. In the methods for treating a disease or a condition associated with or mediated by a glutamate receptor or an NK2 receptor, the patient may or may not be being treated by psychotherapy concurrently with the treatment.

Another aspect of the invention is methods of treatment of mental health disorders comprising the administration of fertilized egg isolate to a patient in need, and uses of fertilized egg isolate for such purposes.

The fertilized egg isolate described herein can be formulated for and administered as various dosage forms, such as those adapted for administration by the oral (including buccal and sublingual), rectal, nasal, topical (including buccal, sublingual, and transdermal), vaginal, rectal, or parenteral (including subcutaneous, intramuscular, intravenous, or intradermal) routes. Particularly preferred are dosage forms adapted for administration by the oral route. Other preferred dosage forms include those adapted for administration by the vaginal or rectal route, such as a suppository.

Fertilized egg isolate formulations adapted for oral administration can be presented as discrete units such as capsules, tablets, microparticles, powders, granules, solutions or suspensions in aqueous or non-aqueous liquids, edible foams or whips, or oil-in-water emulsions or water-in-oil emulsions. The fertilized egg isolate can be combined with a suitable oral, non-toxic pharmaceutically acceptable inert carrier. In the case of capsules, a suitable encapsulator, such as a gelatin sheath, can be used to encapsulate the fertilized egg isolate alone or in combination with suitable non-toxic pharmaceutically acceptable inert carrier(s). In respect of tablets and capsules, for example, suitable carriers can include, but are not limited to, edible carbohydrate, such as, for example, starch or mannitol, flavoring, preservative, dispersants, binders, and coloring agents, and can include fumed silica. The formulation can also be prepared to prolong or sustain the release of the fertilized egg isolate, in accordance with means known to those skilled in the pharmaceutical formulation arts.

An effective dosage for treatment will depend on the patient. Effective dosages can range from about 200 to about 6000 mg/day, or from about 500 to about 4000 mg/day, or from about 750 mg/day to about 3500 mg/day, or from about 800 to 3000 mg/day, or from about 1000 to 2500 mg/day. For example, the effective dosage could be about 2000 mg/day.

The term "treat" means improving the disease or condition of a patient to whom the fertilized egg isolate of the present invention is being administered. This term includes ameliorating the disease or condition, and such amelioration can be determined using standard tests known in the art. The term also includes preventing the disease or condition from occurring or re-occurring, such as in prophylactic or maintenance therapy.

Another aspect of the invention features a method for inhibiting an activity of a glutamate receptor comprising contacting the glutamate receptor with an effective amount of fertilized egg isolate. This method can be performed using an ionotropic glutamate receptor, for example, an AMPA receptor, a kainate receptor or an NMDA receptor.

In addition, the invention features a method for inhibiting an activity of an NK2 receptor comprising contacting the NK2 receptor with an effective amount of fertilized egg isolate.

The activity of a glutamate receptor or an NK2 receptor can be inhibited, for example, by inhibiting binding of the receptor by its endogenous ligand(s) (e.g., glutamate for the glutamate receptors and NKA for the NK2 receptor), or commercially available exogenous ligands, such as AMPA, NMDA, kainate, CGP 39653 or MDL-105,509 for the glutamate receptors, and saredutant for the NK2 receptor. Methods for inhibiting such a binding interactions and for detecting such binding inhibition are known to those skilled in the art, and are also described herein. Activity of the glutamate receptor or NK2 receptor can be inhibiting by 100% or by less than 100% (for example, by 90%, 80%, 70%, 60%, 50%, 40%, 30%, 20% or 10%). Methods for inhibiting the activity of a glutamate receptor or an NK2 receptor can be carried out in vitro (for example, in a cell, cell lysate, or a sample containing a portion of a cell, for example, just the relevant receptor) or in vivo (for example, in a human patient).

According to a further embodiment of the invention, the fertilized egg isolate can be formulated with other compounds which may be useful for treating mental health disorders. For example, the fertilized egg isolate can be formulated with compounds that may inhibit the breakdown of serotonin, such as monoamine oxidase inhibitors.

Still other objects and advantages of the present invention will become readily apparent to those skilled in the art from the detailed description, wherein only the preferred embodiments are described, simply by way of illustration. As will be realized, the invention is capable of other and different embodiments, and its several details are capable of modification in various obvious respects, all without departing from the invention. Accordingly, the description and examples below are to be regarded as illustrative in nature, and not as restrictive.

EXAMPLES

Example 1

Fertilized hen eggs that were 8-9 days old were selected. The whole egg was disinfected with 70% ethanol and left in the fume hood to allow the 70% ethanol to evaporate. The eggs were broken and the contents were dropped through a sterile 1.0 mm mesh. The shells and filtrate were discarded. The retentate, both solid and liquid, was collected and chilled on ice. The retentate was homogenized at 5° C. The homogenate (slurry) was poured into sterile stainless steel trays, frozen, and freeze-dried. The dried product was pulverized with a grinder. Preservatives 0.5% w/w sodium benzoate and 0.2% w/w potassium sorbate were added to the powder, and the mixture was blended. The finished powder was stored at 2-8° C. (short term) or −20° C. (long term).

Example 2

Chicken embryos were harvested at 8 days old from fertilized hen eggs according to the following method:
 (i) 24 brown eggs were received;
 (ii) when cracked open, only 22 of 24 eggs where found fertilized containing the developed embryo (91.6% fertilization rate);
 (iii) embryos were removed and washed (×2) briefly in sterile PBS and immediately frozen at −20° C. in individual 50 mL (milliliter) test tubes;
 (iv) 10 test tubes were then freeze dried in a freeze dryer (shelf temp.=−40° C., condenser temp. −52° C.);
 (v) at the end of the cycle, the individual embryos (while in test tube) were crushed with a sterile glass rod and the resulting powder (1.7 g (grams)) was packaged;
 (vi) the 12 remaining embryos were pooled in a small beaker and blended with a small amount of water using a hand held blender;
 (vii) the resulting slurry was immediately frozen and subsequently freeze dried as above.
Results Once dried, the powder (1.7 g) was dispersed and made homogeneous using a glass rod=Lot# A. Each embryo yielded 0.17 g powder.

The dried slurry (1.6 g) was dispersed and made homogeneous using a glass rod=Lot# B. Each embryo yielded 0.14 g powder (moisture unknown).

Example 3

Sixty fertilized eggs (8 day old embryos) were received. The following is a description of the preparation of both the aqueous and the ether isolates.

All eggs were sprayed with 70% (v/v) ethanol to sterilize the external surface and the eggs were left in the laminar flow hood for the alcohol to evaporate. The eggs were broken and the embryos and the attached clear sac with its clear watery content were carefully separated from the rest of yolk and vascular material. Then, all material, that is, the embryo and clear sacs, was pooled in a beaker that had been chilled on ice. Following the harvest, the material was blended with the help of a hand held blender, resulting in a slurry.

The resulting slurry (approx. 200 mL) was split into two equal halves; one was used for extraction with water and the second for ether extraction.

Aqueous Isolate

To the 100 mL slurry, 100 mL of R.O. water was added and the material was stirred at room temperature for 30 minutes. The material was clarified by centrifugation and the aqueous top layer was collected (200 mL 1.1% solids). The aqueous top layer was then frozen and subsequently freeze dried. The dry powder weighed 1.0 g.

Ether Isolate

To 100 mL of the slurry, 100 mL of previously chilled ether was added. The mixture was shaken at room temperature and then subjected to centrifugation. At the end of the centrifugation period (15 minutes at 5° C.), the top aqueous/ether layer was transferred to a separating funnel and the top ether layer was collected either by siphoning or, after a period of freezing at −20° C. that froze the lower turbid aqueous layer leaving the top clear yellow ether layer unfrozen, decanting.

The lower aqueous layer was extracted again with an equal volume of ether as described above and the process was repeated three times. The ether isolate was then concentrated and dried in the Rotavap™ to a small volume (approximately 1 mL). The sample was kept at 5° C.

Example 4

Four hundred twenty fertilized eggs (8-9 day old embryos) were sprayed with 70% (v/v) ethanol to sterilize the external surface as much as possible and the eggs were left in a fume hood for the alcohol to evaporate.

The eggs were broken (62 out of 420 were found unfertilized, fertilization rate=85.2%) and the embryos and their attached clear sac with its clear watery content were carefully separated from the rest of yolk and vascular material and all material, that is, the embryo and clear sacs, was pooled in a beaker that had been chilled on ice. The harvested material (approx. 2 L) was kept at 5° C.

Aqueous Isolate

Following the harvest, the material was blended with a hand-held blender that produced a slurry. The resulting slurry (approx. 2 L) was passed through a metal sieve (MESH no. 20). The filtrate was further clarified with a paper filter pad and DE 6000. The cake left on the filter pad was discarded. To the filtrate, Superflow DE™ was added and the material was further clarified by passing through a filter pad. All filtration was done using a Buchner funnel at bench scale level. The majority (about 1200-1300 mL) of the resulting filtrate was separated and immediately frozen in trays for freeze drying (1.9% solids). The remaining 500 mL was mixed with an equal volume of previously chilled ethyl ether in a 1 L bottle and kept at 5° C. until separation of the two layers.

Ether Isolate

To 500 mL of the slurry, 500 mL of previously chilled ether was added, the mixture was shaken at room temperature and then subjected to centrifugation. At the end of the centrifugation period (15 minutes at 5° C.) the top aqueous/ether layer was transferred to a separating funnel and the top ether layer was collected either by siphoning or after a period of freezing at −20° C. that will freeze the lower turbid aqueous layer, leaving the top clear yellow ether layer to be decanted.

The lower aqueous layer was extracted again with 300 mL of ether as described above and the isolates were pooled in a round-bottom, previously chilled flask. The ether isolate was then concentrated and dried in the Rotavap™ to a small volume. The sample was kept at 5° C.

Example 5

Fertilized Egg Isolate A

To produce fertilized egg Isolate A, 8-9 day old whole fertilized hen eggs were disinfected with 70% ethanol and left in a fume hood to allow the solvent to evaporate. The eggs were then broken and the contents dropped on or through a sterile 1.0 mm mesh. The shells and filtrate were discarded. The retentate, which comprised the embryo, clear sac, and all or a substantial part of the albumen and consisted of solid and semi-solid and/or liquid portions, was chilled on ice and then homogenized at 5° C. The homogenate (slurry) was poured into sterile stainless steel trays, and freeze-dried. The dried product was pulverized in a grinder to give Isolate A. To Isolate A, the preservatives sodium benzoate (0.5% w/w) and potassium sorbate (0.2% w/w) were added and the mixture was blended. The finished powder was stored at 2-8° C. (short term) or −20° C. (long term).

HPLC Analysis

Figure 6:
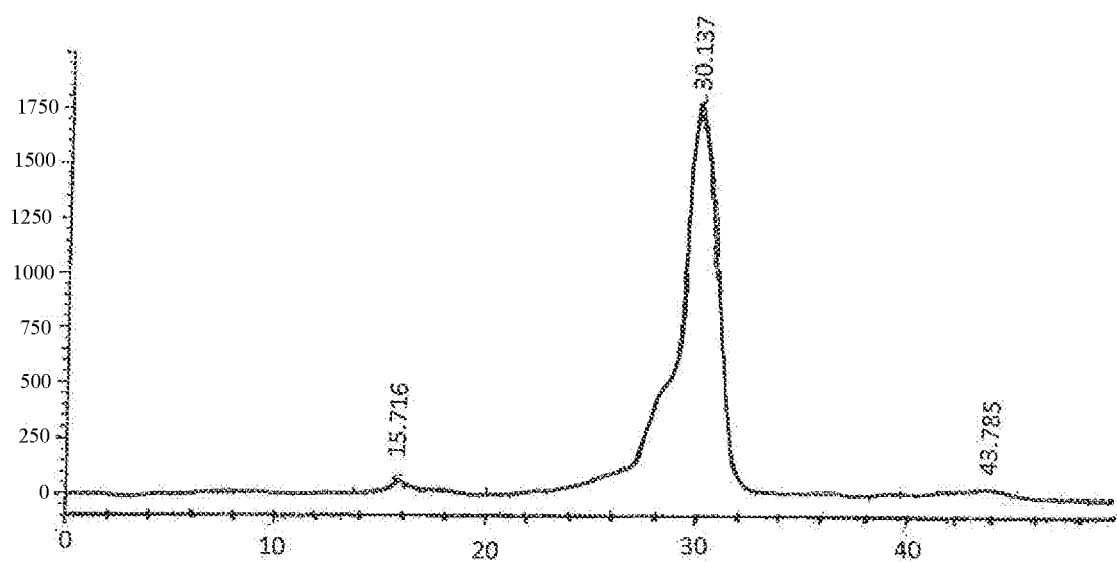
FIG. 6 shows an HPLC chromatogram of a fertilized egg isolate according to embodiments of the present invention.
Figure 8:
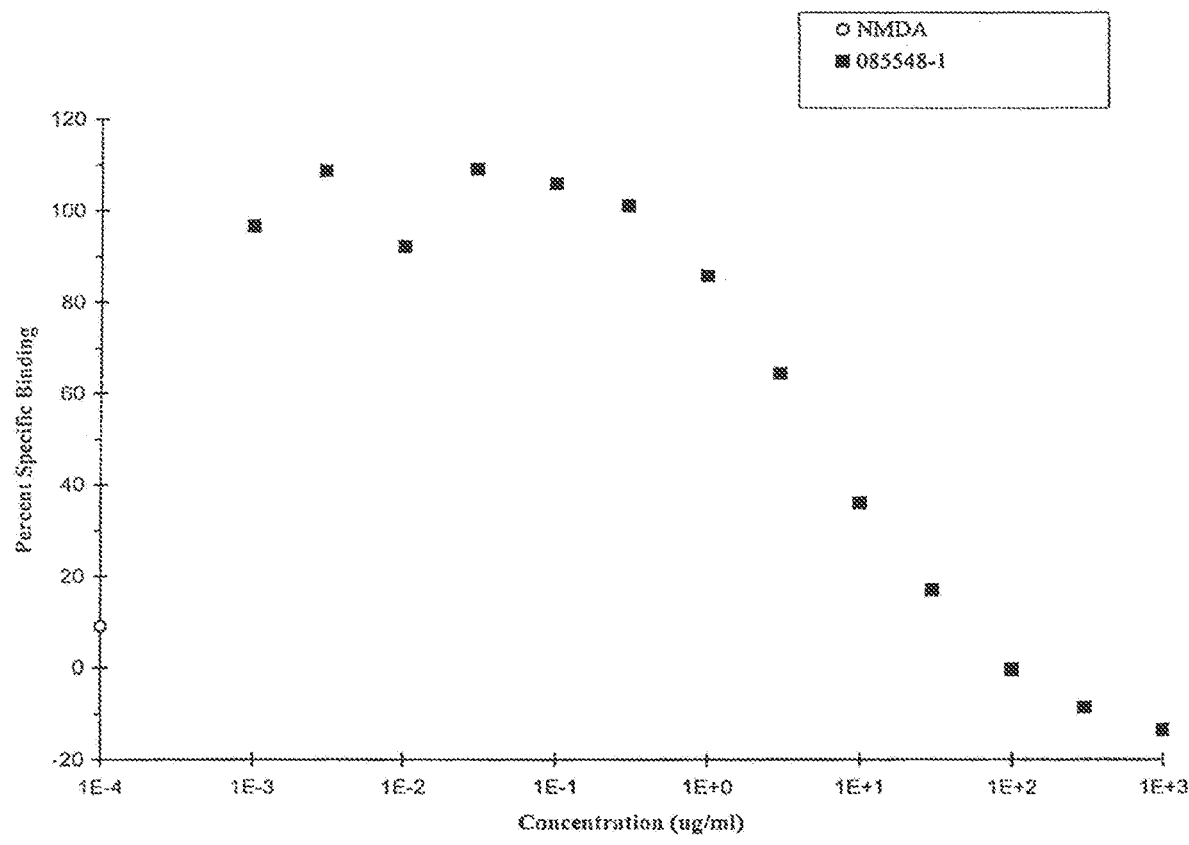
FIG. 8 shows a graph of the effect of various concentrations of the fertilized egg isolate Sample #20 Top Isolate (μg/mL) on binding of radio-labeled CGP 39653 to the agonist site (ionotropic) of the NMDA glutamate receptor (measured as percent of specific binding) as well as the $IC_{50}$ and $K_i$ for NMDA and Sample #20 Top Isolate.
Figure 9:
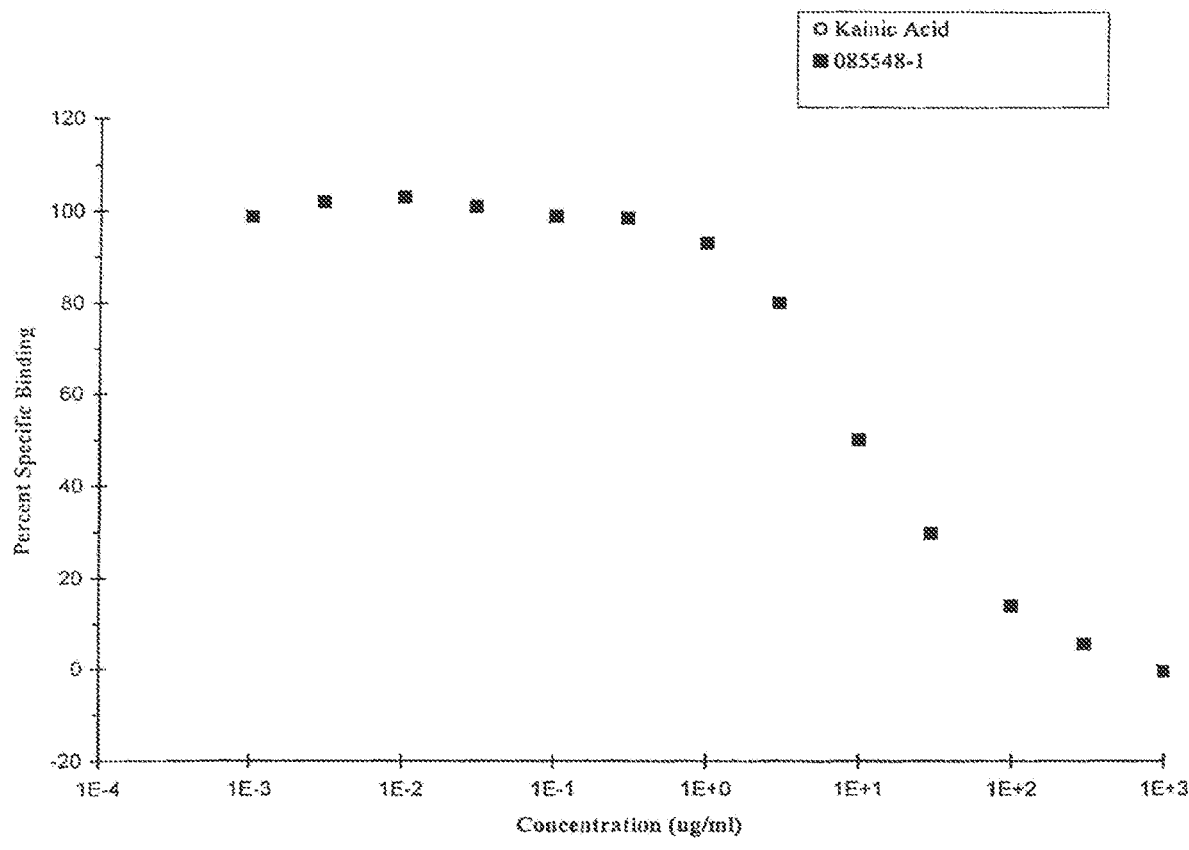
FIG. 9 shows a graph of the effect of various concentrations of the fertilized egg isolate Sample #20 Top Isolate (µg/mL) on binding of radio-labeled kainic acid to the kainate site (ionotropic) of the kainate glutamate receptor (measured as percent of specific binding) as well as the $IC_{50}$ and $K_i$ for kainic acid and Sample #20 Top Isolate.
Figure 10:
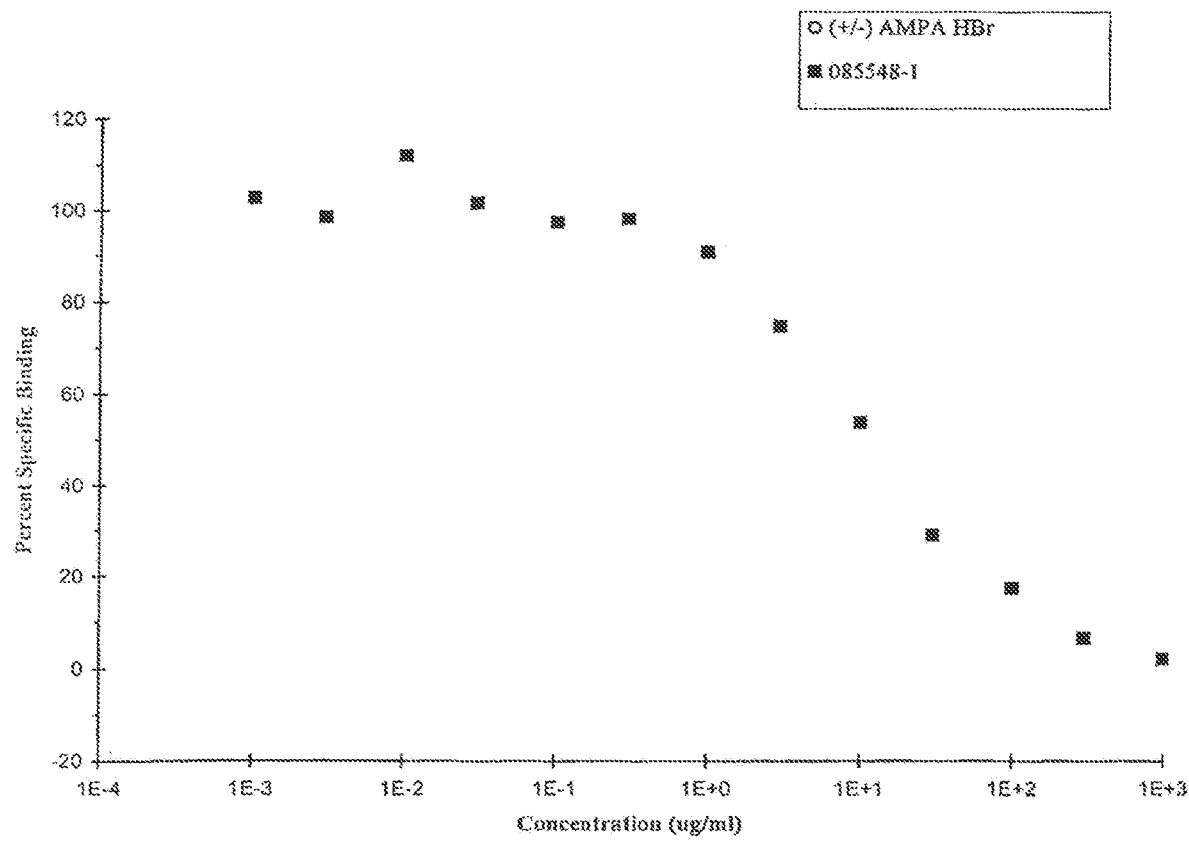
FIG. 10 shows a graph of the effect of various concentrations of the fertilized egg isolate Sample #20 Top Isolate (µg/mL) on binding of radio-labeled α-amino-3-hydroxyl-5-methyl-4-isoxazole-propionate (AMPA) to the AMPA site (ionotropic) of the AMPA receptor (measured as percent of specific binding) as well as the $IC_{50}$ and $K_i$ for (+/−) AMPA HBr and Sample #20 Top Isolate.
Figure 11:
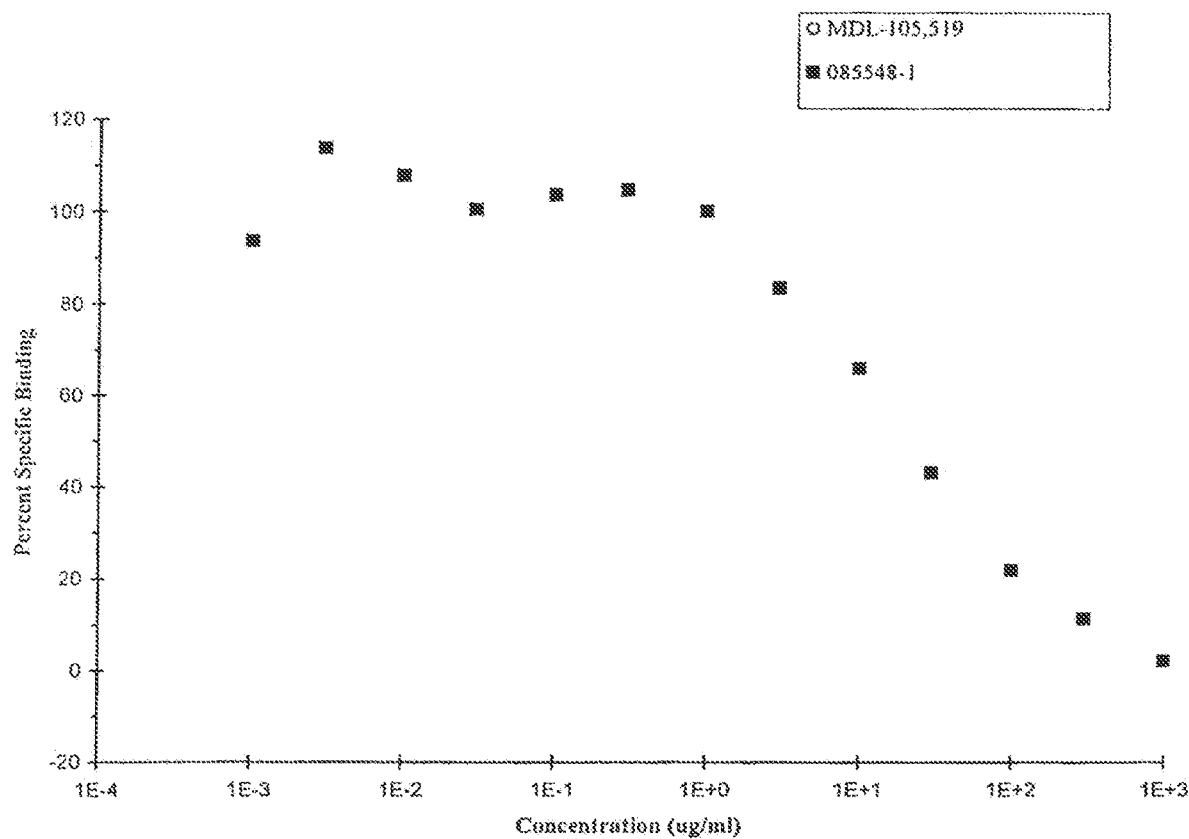
FIG. 11 shows a graph of the effect of various concentrations of the fertilized egg isolate Sample #20 Top Isolate (µg/mL) on binding of radio-labeled MDL-105,519 to the glycine site that is strychnine-insensitive (ionotropic) of the NMDA glutamate receptor (measured as percent of specific binding) as well as the $IC_{50}$ and $K_i$ for MBL-105,519 and Sample #20 Top Isolate.
Figure 12:
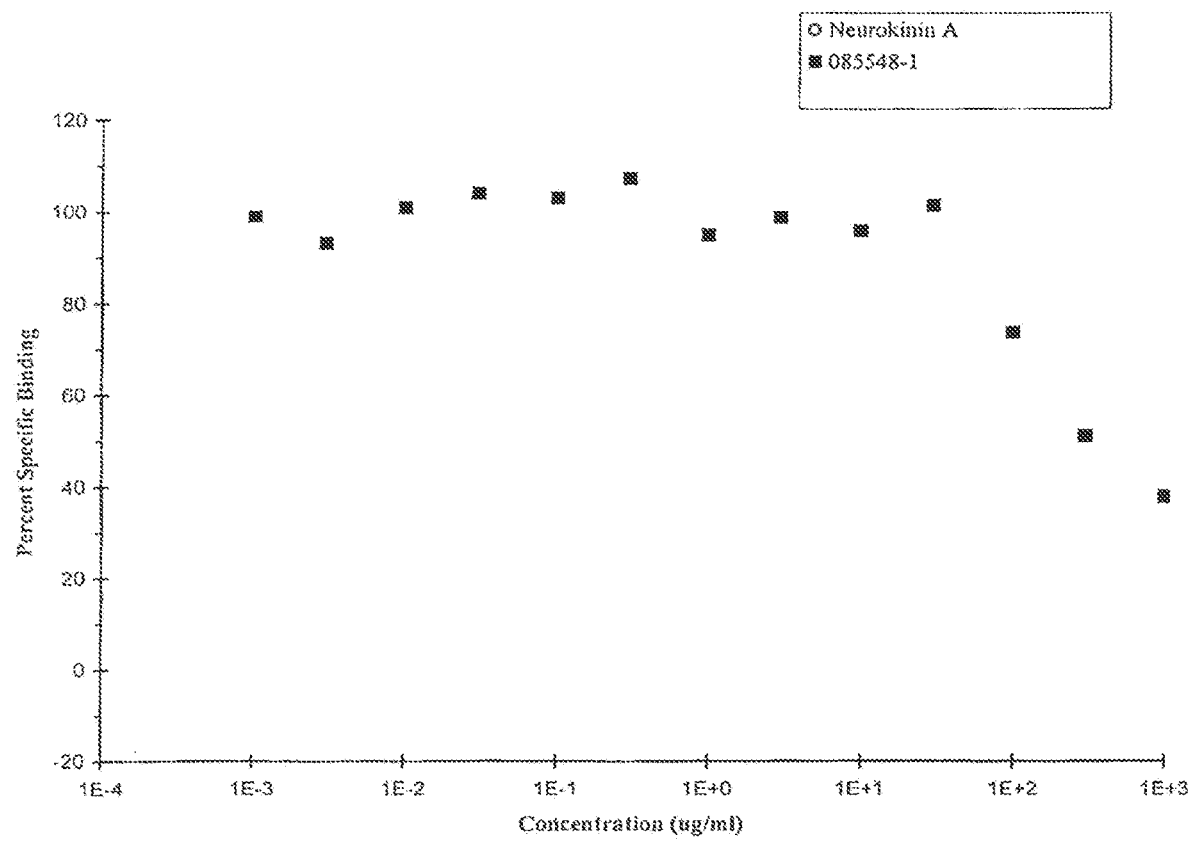
FIG. 12 shows a graph of the effect of various concentrations of the fertilized egg isolate Sample #20 Top Isolate (µg/mL) on binding of neurokinin A (NKA) to the NK2 receptor (measured as percent of specific binding) as well as the $IC_{50}$ and $K_i$ for neurokinin A and Sample #20 Top Isolate.

The finished powder containing fertilized egg Isolate A was analyzed by High Performance (or Pressure) Liquid Chromatography (HPLC). The results were quantified using a multiple-wave absorption detector. Absorption was read at 215 nm. A Pharmacia Superdex 200 10/300GL size exclusion column (10 mm i.d.×300 mm) was used for fractionation. The separation range of the column was 10 kDa-600 kDa. The column was equilibrated with 20 mM phosphate+ 0.3 M NaCl, pH 7.5. The sample was analyzed at a flow rate of 0.5 mL/min. A representative chromatogram is shown at FIG. 6.

Certificate of Analysis

The finished powder containing Isolate A was also subjected to standard analytical procedures to measure purity and the content of protein, fat, ash, moisture, and various contaminants. A representative sample of the results is shown at FIG. 7.

Formulation A Capsules

In order to prepare capsules of Formulation A, 4000.0 g (+/−2%) of the finished powder containing Isolate A, sodium benzoate (0.5% w/w) and potassium sorbate (0.2% w/w) was mixed with 40 g (+/−2%) of fumed silica using geometric dilution. The mixture was sifted, and the mixing and sifting were repeated, resulting in Formulation A. The Formulation A mixture was encapsulated using Mini-Cap 300#0 white capsules to a target fill weight of 505 mg to produce Formulation A capsules.

Example 6

Study of Formulation a for Treatment of Major Depressive Disorder (MDD) and Disorders/Symptoms Related Thereto The efficacy and safety of a fixed dose of Formulation A to treat mental disorders, such as MDD and related disorders and symptoms, were studied. This study included evaluation of the effect of Formulation A on reducing symptoms of anxiety, improving quality of life, and improving symptoms of sexual dysfunction.

Description of Evaluation Techniques

Hamilton Depression Rating Scale-17 Item—"HAM-D" or "HAM-D 17"

This is a leading rating scale used in North America for evaluating depression in a patient. The total scores are interpreted as follows: very severe, >23; severe, 19-22; moderate, 14-18; mild, 8-13; and no depression, 0-7.

Hamilton Anxiety Rating Scale-14 Item—"HAM-A"

This rating scale evaluates the level of anxiety in a patient. The score levels are interpreted as follows: <17, mild; 18-24, mild to moderate; and 25-30, moderate to severe.

Montgomery-åsberg Depression Rating Scale—"MADRS"

This is a leading rating scale used in North America for evaluating depression in a patient. The following mean scores correlate with global severity measures, according to a study: very severe, 44; severe, 31; moderate, 25; mild, 15; and recovered, 7.

Beck Depression Inventory—"BDI"

This is a commonly employed measure of depressive symptoms typically used as a self-assessment instrument. The total score is the simple sum of the 21 item scores. Generally, a score <9 indicates no or minimal depression, 10-18 indicates mild-to-moderate depression, 19-29 indicates moderate-to-severe depression, and >30 indicates severe depression. However, a score of 0-4 may suggest possible denial of depression and a score of 40-63 may suggest possible exaggeration of depression or a histrionic or borderline personality disorder.

Arizona Sexual Experience Scale—"ASEX"

This is a 5-item rating scale that quantifies sex drive and evaluates levels of arousal, vaginal lubrication/penile erection, ability to reach orgasm, and satisfaction from orgasm.

Possible total scores range from 5 to 30, with the higher scores indicating more sexual dysfunction.

General Health Questionnaire Scoring—"GHQ"

The quality of life dimension may have been assessed with the Short-Form 36 (SF-36). This questionnaire evaluates such problems as, the ability to concentrate, feelings of worry, low self-confidence, feelings of low self-worth, unhappiness, and depression. The scoring is as follows:

Likert Scale 0, 1, 2, 3 from left to right.

12 items, 0 to 3 each item.

Score Range 0 to 36.

Scores vary by study of population. Scores about 11-12 are typical.

Score >15 evidence of distress.

Score >20 suggests severe problems and psychological stress.

Diagnostic and Statistical Manual of Mental Disorders-IV-Text Revision—"DSM-IV TR"

This is the standard diagnostic manual in North America for mental health professionals that comprehensively classifies mental disorders and provides widely accepted criteria for diagnosing them based on the best empirical evidence available.

The primary effect measured was the repeated analysis of variance with the score on the HAM-D as the outcome variable. Secondary effect measures included the CGI-S and CGI-I, MADRS, SF36, BDI, HAMA and ASEX.

Description of Study

An open-label study was carried out at Mount Sinai Hospital (MSH) in Toronto, Ontario, Canada. Patients were recruited by media advertisement, referral from the MSH outpatient program and from other clinical centres.

This protocol describes an open pilot study to investigate Formulation A's potential antidepressant activity. The goal of the pilot study was to demonstrate that Formulation A has the potential to significantly improve MDD beyond the levels of the known placebo effect well established in other trials and that Formulation A is an acceptable treatment in this patient population. Secondary aims of this pilot study were to evaluate the effect of Formulation A on reducing symptoms of anxiety and improving quality of life.

Each patient was screened for MDD using DSM-IV TR criteria and the HAM-D. Once entered, they were assigned to the open-label Formulation A study for a period of 8 weeks. The patients were further assessed by a global measure, the CGI severity (GCI-S) and improvement (CGI-I) scales. Side effects were systematically evaluated using The Udvalg for Kliniske Undersøgelser (UKU) Side Effect Rating Scale (Lingjaerde). Secondary measures of depressive symptoms were the Montgomery Asberg Depression Rating Scale (MADRS) and the Beck Depression Inventory (BDI) as self assessment instruments. The quality of life dimension was assessed with the Short-Form 36 (SF-36). Anxiety was assessed using the 14 item HAM-A.

In the fixed dose open trial, patients were treated for depression based on standard treatment protocols for depression. The investigators determined the severity of depression with the rating scales at baseline, and at repeated visits at weeks (W) 2, 4, 6, and at week 8. In intervening weeks patients were seen in brief clinical assessments (V) to evaluate depression and medication tolerance.

Dosage of Formulation A

The dosage of Formulation A was about 2000 mg/day (2 Formulation A capsules of about 500 mg each, taken orally twice a day).

Inclusion Criteria of Patients

For inclusion in this study, patients had to have met a number of inclusion criteria, including criteria (i)-(vi), as described below.

(i) A clinical diagnosis fulfilling DSM-IV TR criteria for major depressive disorder, single episode or recurrent.

(ii) 17—Item Hamilton Depression Rating Scale (HAM-D 17-item) total score at baseline of 18 or higher.

(iii) Males/Females 18-65 years of age who require a new or a change in their medication treatment for diagnosed major depression. Treatment decisions were made solely upon the clinician's judgment of the standard of care appropriate to that patient. However augmentation strategies are not permitted during the 8 week trial.

(iv) English language literacy.

(v) Signed written informed consent obtained.

(vi) A negative pregnancy test at screening.

Exclusion Criteria

Patients were excluded from this study if they met a number of exclusion criteria, including criteria (i)-(xiii), as described below.

(i) Any other DSM IV TR diagnosis including a clinical diagnosis of depression other than DSM-IV TR MDD (single episode/recurrent, e.g., chronic depression and/or refractory depression were excluded).

(ii) Judged to be at significant risk for suicide (HAMD suicide item >1) or having a history suggesting significant current potential for self harm.

(iii) Any antidepressant medication other than Formulation A.

(iv) Subjects who were taking and unable or unwilling to discontinue natural health products used for depression.

(v) Women who were pregnant, breast-feeding, intending to become pregnant in the next 12 months or on insufficient contraceptive protection.

(vi) Clinically significant organ system diseases, e.g., cardiovascular, hepatic, renal, endocrine, gastrointestinal, metabolic, or other systemic diseases.

(vii) Course of electroconvulsive therapy (ECT) during the observational period.

(viii) Suffer from a major neurological condition (i.e., Parkinson's disease, Huntington's disease), cerebrovascular disease (i.e., stroke), metabolic conditions (i.e., Vitamin B12 deficiency), autoimmune conditions (i.e., systematic lupus erythematosus), viral or other infections (i.e., hepatitis, mononucleosis, human immunodeficiency), or cancer.

(ix) Clinical or subclinical hypo/hyper thyroidism (e.g., elevated TSH).

(x) Allergies to poultry or eggs.

(xi) Subjects who were receiving psychotherapy or who began psychotherapy during the trial.

(xii) Subjects with clinically significant abnormal laboratory results from screening blood and urinalysis.

(xiii) Subjects who became significantly worse during the washout period.

Study Design

This was a single site, open-label, randomised study of 25 patients designed to validate the efficacy and safety of Formulation A monotherapy.

The trial consisted of an 8 week evaluation period preceded if necessary by a 2 week antidepressant washout period.

Screening

Once the physician and/or research coordinator fully informed the subject of the study, the nature of the treatment, and the other options available to them, and the subject signed the informed consent document, the physician made the clinical DSM IV TR diagnosis and administered the HAM-D 17. Eligible subjects then had a medical, psychiatric history and concomitant therapy review followed by a physical examination. In addition, baseline laboratory tests were taken by the research coordinator including urine (Routine & Microscopic), CBC differential and platelets, electrolytes, bilirubin, BUN, creatinine, TSH, Liver Function Tests, Serum creatinine, and ECG. A pregnancy screen for female patients was obtained by hCG blood test. Pregnant patients and those with clinically significant abnormal laboratory tests were excluded.

Week 0

Patients returned for a Baseline visit (Week 0) and were assigned to Formulation A monotherapy by the physician. Patients who were depressed and on a current but ineffective antidepressant were offered the switch to Formulation A.

Following Weeks

Following the initial assessment and initiation of Formulation A therapy (V1 and V2) the scheduled visits occurred every week for 8 weeks (W2-W8, V3-V6). Those who were on another antidepressant drug and who chose to enter the study entered a 1-2 week washout period before beginning the 8 week active drug trial. The washout period was at the clinical discretion of the physician. During this time, patients were monitored in a visit one week into the washout by the psychiatrist and further monitored by phone by the study coordinator mid-week. It is recognized that depression may worsen during the washout period. However, if the prior drug was ineffective or partially ineffective the risks that a 1-2 week delay will significantly induce depressive decline in this protocol are not substantially greater than usual care as long as subjects are carefully monitored during this time and appropriate intervention instituted as necessary. If Formulation A were not to be an effective antidepressant for a particular patient, the patient may be at risk for undue prolongation of depression. However, depression is a chronic disorder which is generally present for months prior to being diagnosed or treated so an additional 8 weeks in the presence of careful monitoring together with institution of Formulation A, a potentially effective medication, should not be substantially different from standard care. Moreover, standard care, as already discussed, is only effective in about 60% of patients and therefore often requires the same possible reevaluations and drug alterations.

At V2 (may be combined with V1 (W0)) to V6 (W8), the following procedures were performed by the supervising psychiatrist (PI) and/or the research coordinator:

Weight
Height
Vital Signs
Hamilton Depression Rating Scale (17 item) (HAM-D 17) (Hamilton 1967).
Clinical Global Impression (CGI-S, CGI-I) (Guy)
Montgomery-Asberg Depression Rating Scale (MADRS) (Montgomery)
Beck Depression Inventory Scale (BDI) (10).—Quality of Life (SF-36) (Ware).
Hamilton rating scale for anxiety (HAMA) (Hamilton 1959)
Udvalg for Kliniske Undersogelser (UKU) (Lingjaerde) (Reporting of Adverse Events) (except at V2)
Medication Compliance (except at V2)

Study visits were estimated at about one hour with the exception of the baseline visit which may have taken 2 hours.

If subjects became more depressed while in the study they were evaluated by the principal investigator to determine the best clinical approach. If deemed necessary, Formulation A was stopped in favour of another antidepressant treatment. This was a clinical decision made solely on the basis of best practices in the treatment of depression and on the patient's best clinical interests.

General supportive contact with the patients by the physician and the research coordinator was permitted, and the contact was generally restricted to answering pertinent questions about the patient's illness course and treatment. No formal psychotherapy was permitted.

Statistical Methods

The primary effect was tested using a repeated analysis of variance with the scores of the HAM-D 17 as the outcome variable. A significant time effect supports the hypothesis. The total anticipated sample size of 25 patients was large enough to detect changes on the HAM-D 17 as follows 0.65 standard deviations (two-tailed one sample P<0.05). The reported standard deviations on the HAM-D-17 were in the range of 4.5 to 6.5. Therefore, the design of this study had 80% power to detect average changes as small as 4.3 points on this 52 point scale. As per inclusion criteria, participants each had a HAM-D 17 score of greater than 17. The Franck criterion for remission was a HAM-D 17 of 9 or under. This study used a more conservative and accepted level of 7 or under. The effect size of 4.3 was sufficiently sensitive to detect clinical improvement from scores greater than 17 to scores less than 10. Positive outcome was statistically based on an expected placebo response rate ranging from 30% to 50% in treatment trials for depression. In this study, a placebo response rate of 40% was assumed. Some analysis of responders and remitters was carried out as appropriate.

Results

A total of 23 patients were entered into the study. Three of the subjects, (#104, #105 and #118) were never treated and hence, their results were not considered analyzable. Of the 20 subjects that received at least one dose of Formulation A, 16 of them completed the 8 week study. The remaining 4 subjects did not complete the 8 week study, but since they each received at least one dose of Formulation A, their results were deemed analyzable. The reasons these 4 subjects did not complete the entire study included non-compliance with the medications and/or appointments, impatience with the results, and the subject leaving the country.

The results for the 20 subjects who received at least one dose of Formulation A are provided in the below tables.

| Total Score Sheet for HAM-D | | | | | | |
|---|---|---|---|---|---|---|
| Screen | Week 0 | Week 2 | Week 4 | Visit 7 | Week 6 | Week 8 |
| Subject #101 | 20 | 14 | | 11 | 7 | 3 |
| Subject #102 | 19 | 15 | 5 | | 2 | 0 |
| Subject #103 | 22 | 7 | 3 | | 5 | 0 |
| Subject #106 | 21 | 4 | 8 | | 10 | 12 |
| Subject #107 | 22 | 17 | 20 | | | |
| Subject #108 | 20 | 14 | 19 | | | |
| Subject #109 | 25 | 16 | 17 | | 20 | 24 |
| Subject #110 | 21 | 10 | 17 | | 8 | 4 |
| Subject #111 | 24 | 20 | 19 | 19 | 23 | 23 |
| Subject #112 | 29 | 8 | 5 | | 2 | 0 |
| Subject #113 | 33 | 13 | 9 | | 11 | 8 |
| Subject #114 | 29 | 13 | 19 | | 22 | 30 |
| Subject #115 | 32 | 8 | 13 | | 5 | 6 |
| Subject #116 | 19 | 17 | 24 | | 17 | 24 |
| Subject #117 | 23 | 11 | 9 | | 8 | |
| Subject #119 | 23 | 23 | 20 | | 13 | 10 |
| Subject #120 | 23 | 5 | | | | |
| Subject #121 | 23 | 11 | 8 | | 6 | 3 |
| Subject #122 | 32 | 22 | 16 | | 23 | 16 |
| Subject #123 | 24 | 19 | 12 | | 10 | 11 |

| Total Score Sheet for GHQ | | | | | | |
|---|---|---|---|---|---|---|
| Screen | Week 0 | Week 2 | Week 4 | Visit 7 | Week 6 | Week 8 |
| Subject #101 | 15 | 27 | | 14 | 11 | 3 |
| Subject #102 | 22 | 11 | 3 | | 0 | 0 |
| Subject #103 | 18 | 9 | 13 | | 2 | 2 |
| Subject #106 | 22 | 10 | 10 | | 6 | 10 |
| Subject #107 | 27 | 12 | 9 | | | |
| Subject #108 | 27 | 19 | 17 | | | |
| Subject #109 | 25 | 16 | 16 | | 17 | 20 |
| Subject #110 | 28 | 13 | 16 | | 9 | 8 |
| Subject #111 | 26 | 15 | 20 | 21 | 21 | 20 |
| Subject #112 | 30 | 15 | 9 | | 4 | 0 |
| Subject #113 | 34 | 13 | 12 | | 5 | 2 |
| Subject #114 | 33 | 25 | 22 | | 22 | 28 |
| Subject #115 | 31 | 2 | 7 | | 5 | 8 |
| Subject #116 | 32 | 26 | 25 | | 25 | 24 |
| Subject #117 | 24 | 14 | 7 | | 8 | |
| Subject #119 | 31 | 19 | 27 | | 20 | 8 |
| Subject #120 | 23 | 8 | | | | |
| Subject #121 | 35 | 7 | 1 | | 1 | 1 |
| Subject #122 | 31 | 23 | 10 | | 23 | 15 |
| Subject #123 | 26 | 17 | 11 | | 4 | 2 |

| Total Score Sheet for MADRS | | | | | | |
|---|---|---|---|---|---|---|
| Screen | Week 0 | Week 2 | Week 4 | Visit 7 | Week 6 | Week 8 |
| Subject #101 | 34 | 24 | | 28 | 10 | 6 |
| Subject #102 | 30 | 18 | 10 | | 0 | 2 |
| Subject #103 | 28 | 10 | 4 | | 2 | 2 |
| Subject #106 | 30 | 14 | 14 | | 18 | 24 |
| Subject #107 | 38 | 28 | 28 | | | |
| Subject #108 | 20 | 18 | 22 | | | |
| Subject #109 | 28 | 23 | 20 | | 28 | 26 |

-continued

Total Score Sheet for MADRS

| Screen | Week 0 | Week 2 | Week 4 | Visit 7 | Week 6 | Week 8 |
|---|---|---|---|---|---|---|
| Subject #110 | 28 | 16 | 36 | | 14 | 10 |
| Subject #111 | 46 | 40 | 40 | 40 | 32 | 36 |
| Subject #112 | 38 | 16 | 10 | | 10 | 2 |
| Subject #113 | 46 | 16 | 18 | | 14 | 6 |
| Subject #114 | 42 | 26 | 38 | | 38 | 44 |
| Subject #115 | 32 | 12 | 12 | | 10 | 10 |
| Subject #116 | 36 | 42 | 44 | | 34 | 46 |
| Subject #117 | 36 | 22 | 10 | | 6 | |
| Subject #119 | 38 | 34 | 34 | | 18 | 10 |
| Subject #120 | 32 | 6 | | | | |
| Subject #121 | 38 | 14 | 6 | | 6 | 4 |
| Subject #122 | 44 | 38 | 22 | | 32 | 24 |
| Subject #123 | 30 | 28 | 22 | | 14 | 16 |

Total Score Sheet for BDI-21

| Screen | Week 0 | Week 2 | Week 4 | Visit 7 | Week 6 | Week 8 |
|---|---|---|---|---|---|---|
| Subject #101 | 27 | 25 | | 27 | 17 | 10 |
| Subject #102 | 25 | 13 | 6 | | 0 | 1 |
| Subject #103 | 26 | 14 | 10 | | 8 | 8 |
| Subject #106 | 30 | 12 | 7 | | 12 | 40 |
| Subject #107 | 33 | 28 | 26 | | | |
| Subject #108 | 32 | 14 | 20 | | | |
| Subject #109 | 29 | 23 | 24 | | 20 | 25 |
| Subject #110 | 29 | 22 | 24 | | 13 | 8 |
| Subject #111 | 32 | 28 | 27 | 33 | 27 | 27 |
| Subject #112 | 37 | 21 | 10 | | 9 | 1 |
| Subject #113 | 53 | 23 | 22 | | 18 | 3 |
| Subject #114 | 54 | 40 | 52 | | 52 | 59 |
| Subject #115 | 39 | 13 | 16 | | 3 | 4 |
| Subject #116 | 38 | 37 | 37 | | 42 | 40 |
| Subject #117 | 24 | 20 | 11 | | 7 | |
| Subject #119 | 35 | 36 | 40 | | 24 | 18 |
| Subject #120 | 26 | 1 | | | | |
| Subject #121 | 43 | 10 | 4 | | 3 | 3 |
| Subject #122 | 55 | 38 | 25 | | 46 | 27 |
| Subject #123 | 33 | 34 | 22 | | 5 | 10 |

Total Score Sheet for HAM-A

| Screen | Week 0 | Week 2 | Week 4 | Visit 7 | Week 6 | Week 8 |
|---|---|---|---|---|---|---|
| Subject #101 | 15 | 9 | | 8 | 7 | 3 |
| Subject #102 | 13 | 8 | 2 | | 0 | 1 |
| Subject #103 | 8 | 7 | 2 | | 0 | 2 |
| Subject #106 | 21 | 5 | 5 | | 5 | 10 |
| Subject #107 | 12 | 7 | 13 | | | |
| Subject #108 | 15 | 8 | 11 | | | |
| Subject #109 | 17 | 12 | 13 | | 18 | 14 |
| Subject #110 | 14 | 8 | 9 | | 2 | 5 |
| Subject #111 | 33 | 29 | 24 | 32 | 23 | 24 |
| Subject #112 | 22 | 10 | 4 | | 1 | 2 |
| Subject #113 | 35 | 22 | 14 | | 4 | 3 |
| Subject #114 | 24 | 10 | 18 | | 21 | 21 |
| Subject #115 | 25 | 10 | 12 | | 4 | 5 |
| Subject #116 | 12 | 13 | 15 | | 12 | 16 |
| Subject #117 | 21 | 10 | 8 | | 7 | |
| Subject #119 | 13 | 19 | 15 | | 13 | 6 |
| Subject #120 | 14 | 4 | | | | |
| Subject #121 | 24 | 9 | 3 | | 4 | 2 |
| Subject #122 | 43 | 31 | 21 | | 32 | 22 |
| Subject #123 | 23 | 27 | 14 | | 8 | 10 |

Total Score Sheet for ASEX

| Screen | Week 0 | Week 2 | Week 4 | Visit 7 | Week 6 | Week 8 |
|---|---|---|---|---|---|---|
| Subject #101 | 12 | 14 | | 12 | 13 | 13 |
| Subject #102 | 21 | 23 | 19 | | 19 | 15 |
| Subject #103 | 12 | 12 | 17 | | 17 | 13 |
| Subject #106 | 10 | 9 | 7 | | 7 | 10 |
| Subject #107 | 15 | 14 | 16 | | | |
| Subject #108 | 15 | 11 | 12 | | | |
| Subject #109 | 17 | 15 | 17 | | 19 | 19 |
| Subject #110 | 26 | 25 | 28 | | 28 | 27 |
| Subject #111 | 28 | 28 | 28 | 28 | 28 | 28 |
| Subject #112 | 11 | 13 | 11 | | 11 | 9 |
| Subject #113 | 28 | 28 | 28 | | 28 | 9 |
| Subject #114 | 28 | 28 | 28 | | 30 | 30 |
| Subject #115 | 19 | 17 | 17 | | 11 | 15 |
| Subject #116 | 11 | 10 | 11 | | 12 | 12 |
| Subject #117 | 14 | 12 | 18 | | 16 | |
| Subject #119 | 30 | 30 | 28 | | 30 | 30 |
| Subject #120 | 19 | 15 | | | | |
| Subject #121 | 18 | 26 | 12 | | 22 | 10 |
| Subject #122 | 26 | 14 | 15 | | 30 | 12 |
| Subject #123 | 22 | 20 | 20 | | 16 | 20 |

Response Rate and Intensity of Response

The following definitions were used to assess each subject's response to treatment with Formulation A. A "responder" or "ever-responder" is a subject with at least 50% improvement on the Hamilton Depression Rating Scale (HAM-D score) as compared to baseline score at any time during the study. A "clinical responder" is a subject meeting the "responder" criteria who, in the opinion of the Principal Investigator has a positive clinical outcome. An "end of study responder" is a subject meeting response criteria at the end of the study (or at last observation). "Remission" is a reduction of the HAM-D score to less than 8.

The above study showed that of the 20 subjects who received at least one dose of Formulations A, 15 of them (75%) were ever-responders, and 14 of them (70%) were clinical responders. In addition, among the 16 subjects who completed the 8 week study, the number of ever-responders was 13/16 (81.3%) and the number of clinical responders was 12/16 (75%). In addition, of the 16 subjects who completed the study, the overall drop in HAM-D score (including non-responders) was significant at 56.08%. The drop in HAM-D score among the ever-responders who completed the 8 week study was higher, at 68.1%, a figure well beyond the minimal 50% drop rate require for an ever-response.

Note should be made of two subjects whose response was influenced by environmental circumstances. Subject #114, who was not included among the clinical responders, was responsive by week 2 when her HAM-D score fell by more than 50% on Formulation A; but external factors intervened. She began to encounter medical problems (not related to Formulation A) and difficulty at work when she applied for disability insurance. These environmental factors completely overtook her good emotional response to Formulation A.

Based on the strict criterion of a 50% reduction in the HAM-D score, subject #106 would not have been considered a responder at week 8 because at that time her score was 12, just short of a 50% drop from her entry Score of 21. Throughout the 8 week trial, however, subject #106 did respond with scores of 4 (week 2), 8 (week 4) and 10 (week 6) In fact, during the study, subject #106 was deemed to be a clinical responder by the PI and was entered into the Extension Study (see Example 7) where scores of 1, 11, 7 and 9 were recorded. After starting the Extension Study, subject #106 was faced with considerable family turmoil which disrupted her positive response to Formulation A. When this turmoil subsided she continued to maintain responsiveness to Formulation A. No medication can completely offset the traumatic effects of environmental circumstances. Formulation A may well have ameliorated the emotional trauma of those circumstances for subject #106.

Remission Rate

Not all ever-responders went into remission and not everyone who went into remission remained there until the end of the 8 week study. Nine of the 15 ever-responders (60%) went into remission at some point during the 8 week study. Seven of those nine subjects (77.8%; or 46.7% of all study participants) who achieved remission remained in remission by the end of the 8 week study.

The table below delineates all those study participants who went into remission and all who stayed in remission. Checkmarks indicate that the subject went into remission or had sustained remission, while X marks indicate that the subject did not go into remission or did not have sustained remission to week 8 of the study.

| Subject | Remission at any time | Remission Sustained to 8 Weeks |
|---|---|---|
| 101 | ✓ | ✓ |
| 102 | ✓ | ✓ |
| 103 | ✓ | ✓ |
| 106 | ✓ | X |
| 110 | ✓ | ✓ |
| 112 | ✓ | ✓ |
| 113 | X | X |
| 114 | X | X |
| 115 | ✓ | ✓ |
| 117 | X | X |
| 119 | X | X |
| 120 | ✓ | withdrew |
| 121 | ✓ | ✓ |
| 122 | X | X |
| 123 | X | X |
| | N ever in remission = 9 (60%) | N in sustained remission = 7 (46.7%) |

In addition, a major secondary outcome, reduction in anxiety, was experienced by all of the ever-responders except one. These results show that Formulation A is effective in the treatment of major depressive disorder and anxiety. Furthermore, there were no serious side-effects attributable to the drug. There was no increase in weight, nor was there a diminution in sexual function in subjects participating in the study.

Example 7

The positive efficacy and safety results of the study described in Example 6 necessitated an Extension Study. Ten subjects from the study described in Example 6 were entered into the Extension Study. The Extension Study was open only to those subjects from the study described in Example 6 who were clinical responders at the end of that 8 week study. Formulation A was administered as described in Example 6 and the subjects in the Extension Study were analyzed on a monthly basis for 10 months. The below table show the HAM-D scores of the subjects in the Extension Study.

| Month | Subject #102 | Subject #103 | Subject #106 | Subject #110 | Subject #112 | Subject #113 | Subject #115 | Subject #119 | Subject #121 | Subject #123 |
|---|---|---|---|---|---|---|---|---|---|---|
| Visit 1 | 0 | 0 | 12 | 4 | 0 | 8 | 6 | 10 | 3 | 11 |
| Visit 2 | 0 | 2 | 1 | 5 | 2 | 9 | 2 | 10 | 4 | 14 |
| Visit 4 | 1 | 8 | 11 | 3 | 1 | 10 | w/d | 3 | 5 | 14 |
| Visit 4 | 0 | 2 | 7 | 1 | 1 | 18 | | 10 | 1 | 3 |
| Visit 5 | 0 | 3 | 9 | 2 | 0 | w/d | | 4 | 5 | |
| Visit 6 | 0 | 1 | 16 | 2 | 1 | | | w/d | | |
| Visit 7 | 0 | w/d | 9 | 2 | 0 | | | | | |
| Visit 8 | 1 | | 6 | 4 | 0 | | | | | |
| Visit 9 | 1 | | 11 | 1 | | | | | | |
| Visit 10 | 2 | | | | | | | | | | w/d = withdrawn from Extension Study

Four of the 10 subjects were withdrawn from the Extension Study due to occurrence of an exclusionary criterion for continuing in the study. The results of this Extension Study showed that all of the subjects in the study were, by definition, responders to Formulation A. Six of the 10 clinical responders (60%) were in remission at the outset of the Extension Study. Eight of the 10 subjects (80%) were in remission at the last date of assessment. Two of the subjects were clinical responders in the initial 8 week study but had not gone into remission until in the Extension Study. Only one subject (#113) who entered the Extension Study as a clinical responder relapsed after entering the Extension Study. The positive efficacy and safety results of the study described in Example 6 and the Extension Study has necessitated a further Extension Study.

Example 8

As described in the above Examples, Formulation A has a demonstrated therapeutic action. Studies have been conducted to investigate the mechanism of action of Formulation A. In particular, studies were conducted to determine inhibition of binding interactions between radioligands and their receptors, or inhibition of radio-labeled enzymes to act on their associated target proteins by Formulation A. The level of inhibition by Formulation A (measured as percent inhibition of specific binding to each receptor by Formulation A) was determined. The testing of inhibition of binding interactions and enzymatic activities was performed in duplicate for each sample at two different concentrations of Formulation A (1.0 µg/mL and 10.0 µg/mL). These concentrations of Formulation A were prepared by dissolving the contents of a capsule of Formulation A in dimethyl sulfoxide and subsequently diluting the solution to either 1.0 µg/mL or 10.0 µg/mL of Formulation A. These diluted solutions were called Isolate A. Radioligand binding assays were then performed using the receptors and enzymes listed in the below table. The average percent inhibition of specific binding at each concentration of Isolate A was determined. The results of this study are shown in the below table.

| Receptor/Enzyme | Percent Inhibition at 1.0 µg/mL of Isolate A | Percent Inhibition at 10.0 µg/mL of Isolate A |
|---|---|---|
| Neurotransmitter Related: | | |
| Adenosine, Non-selective | 4.52 | 12.06 |
| Adrenergic, Alpha 1, Non-selective | −5.01 | −0.56 |
| Adrenergic, Alpha 2, Non-selective | 0.52 | 7.88 |
| Adrenergic, Beta, Non-selective | 3.97 | 17.38 |
| Dopamine Transporter | 4.73 | −1.61 |
| Dopamine, Non-selective | −11.52 | −0.59 |
| GABA A, Agonist Site | 1.11 | 10.58 |
| GABA A, BDZ, alpha 1 site | 3.18 | 11.96 |
| GABA-B | 19.85 | 14.33 |
| Glutamate, AMPA Site (Ionotropic) | 5.79 | 29.05 |
| Glutamate, Kainate Site (Iontropic) | 3.96 | 22.38 |
| Glutamate, NMDA, Agonist Site (Ionotropic) | 1.12 | 34.59 |
| Glutamate, NMDA, Glycine (Strychnine-insensitive site) (Ionotropic) | 5.63 | 27.45 |
| Glycine, strychnine-sensitive | 7.29 | 8.86 |
| Histamine, H1 | −11.22 | −8.21 |
| Histamine, H2 | −0.47 | 3.83 |
| Histamine, H3 | 14.37 | −6.79 |
| Melatonin, Non-selective | −12.91 | −3.64 |
| Muscarinic, M1 (hr) | −4.72 | −17.33 |
| Muscarinic, M2 (h) | 1.52 | 1.19 |
| Muscarinic, Non-selective, Central | −12.00 | −8.66 |
| Muscarinic, Non-selective, Perhpheral | −11.85 | −9.74 |
| Nicotinic, Neuronal (a-BnTx insensitive) | −0.73 | −1.74 |
| Norepinephrine Transporter | 6.12 | 7.68 |
| Opioid, Non-selective | 9.10 | 7.72 |
| Orphanin, ORL1 (h) | −11.04 | −10.55 |
| Serotonin Transporter | −0.81 | 5.46 |
| Serotonin, Non-selective | −1.24 | 5.06 |
| Sigma, Non-selective | 0.38 | 0.60 |
| Steroids: | | |
| Estrogen | 2.23 | 7.46 |
| Testosterone (cytosolic) (h) | 5.80 | 6.16 |
| Ion Channels: | | |
| Calcium Channel, Type L (Dihydropyridine site) | 0.17 | −6.09 |
| Calcium Channel, Type N | 5.01 | 5.02 |
| Potassium Channel, ATP-Sensitive | −1.00 | 2.46 |
| Potassium Channel, $Ca^{2+}$ Act., VI | −0.72 | −1.23 |
| Potassium Channel, I [Kr] (hERG) (h) | −12.25 | −10.99 |
| Sodium, Site 2 | −0.73 | 9.17 |
| Second Messengers: | | |
| Nitric Oxide, NOS (Neuronal-Binding) | −19.63 | −0.04 |
| Prostaglandins: | | |
| Leukotriene, LTB4 (BLT) | −0.39 | −8.11 |
| Leukotriene, LTD4 (CysLT1) | 14.10 | 19.68 |
| Thromboxane A2 (h) | −2.41 | 5.28 |
| Growth Factors/Hormones: | | |
| Corticotropin Releasing Factor, Non-selective | −4.31 | 8.08 |
| Oxytocin | 14.83 | 17.68 |
| Platelet Activating Factor, PAF | −15.15 | 5.99 |
| Thyrotropin Releasing Hormone, TRH | 3.59 | 7.53 |
| Brain/Gut Peptides: | | |
| Angiotensin II, AT1 (h) | −10.80 | −8.76 |
| Angiotensin II, AT2 | 8.82 | 10.55 |
| Bradykinin, BK2 | −18.67 | −6.65 |
| Cholecystokinin, CCK1 (CCKA) | −20.25 | −7.09 |
| Cholecystokinin, CCK2 (CCKB) | −0.31 | −1.74 |
| Endothelin, ET-A (h) | 15.33 | −9.23 |
| Endothelin, ET-B (h) | 19.44 | 26.76 |
| Galanin, Non-selective | 7.94 | 20.49 |
| Neurokinin, NK1 | 19.32 | 13.63 |
| Neurokinin, NK2, (NKA) (h) | 15.62 | 32.15 |
| Neurokinin, NK3 (NKB) | −7.70 | 1.09 |
| Vasoactive Intestinal Peptide, Non-selective | 18.20 | −1.65 |
| Vasopressin 1 | 8.63 | 1.84 |
| Enzymes: | | |
| Decarboxylase, Glutamic Acid | 9.11 | 5.63 |
| Esterase, Acetylcholine | −2.21 | −1.78 |
| Oxidase, MAO-A, Peripheral | −11.09 | −3.83 |
| Oxidase, MOA-B, Peripheral | −18.26 | −15.82 |
| Transferase, Choline Acetyl | 18.06 | 20.00 |

In general, a binding inhibition or an enzymatic activity inhibition of 20% or less is indicative that a given test compound is inactive at that particular receptor binding site or target protein. A binding inhibition or an enzymatic activity inhibition of more than 20% is indicative that the test compound has activity at that particular binding site or enzyme site. The above-described binding inhibition studies showed that Isolate A displaced glutamate from four of its major ionotropic receptors. Binding by radio-labeled AMPA to the AMPA receptor was inhibited by 29.05% in the presence of Isolate A (10 µg/mL). Binding by radio-labeled kainic acid to the kainate receptor was inhibited by 22.38% in the presence of Isolate A (10 µg/mL). Binding by radio-labeled CGP 39653 to the agonist site of the NMDA receptor was inhibited by 34.59% in the presence of Isolate A (10 µg/mL). Binding by radio-labeled MDL-105,519 to the glycine site that is strychnine-insensitive of the NMDA receptor was inhibited by 27.45% in the presence of Isolate A (10 µg/mL). In addition, binding by neurokinin A to the NK2 receptor was inhibited by 32.15% in the presence of Isolate A (10 µg/mL). Additional details regarding the binding inhibition experiments for each of the five above described receptors are provided in the following table.

| Receptor | Radioligand | $K_d$ (M) | Reference Compound | $K_i$ of the Reference Compound (M) |
|---|---|---|---|---|
| Glutamate, AMPA | [$^3$H]AMPA | $2.8 \times 10^{-8}$ | (+/−) AMPA HBr | $2.64 \times 10^{-8}$ |
| Glutamate Kainate | [$^3$H]Kainic Acid | $1.6 \times 10^{-8}$ | Kainic Acid | $1.05 \times 10^{-8}$ |
| Glutamate, NMDA Agonist site | [$^3$H]CGP 39653 | $7 \times 10^{-9}$ | NMDA | $9.63 \times 10^{-6}$ |
| Glutamate, NMDA, glycine (strychnine-insensitive site) | [$^3$H]-MDL-105,519 | $2 \times 10^{-8}$ | MDL-105,519 | $1.72 \times 10^{-8}$ |
| Neurokinin 2 (NK2) | [$^{125}$I]-Neurokinin A | $5 \times 10^{-10}$ | Neurokinin A | $2.53 \times 10^{-10}$ |

The ionotropic glutamate receptors, the NK2 receptor and the neurokinin 1 (NK1) receptor were used in additional receptor binding assays. A one-concentration controlled experiment was performed to assess the ability of various isolates of the contents of a Formulation A capsule to antagonize ligand binding by various glutamate receptors and the NK2 receptor. The AMPA receptor, kainate receptor, the agonist and glycine (strychnine-insensitive) binding sites of the NMDA receptor, as well as the NK2 receptor were studied in this assay. The contents of Formulation A capsules were dissolved using various solvents and extracted using four different processes, as described in detail below. These extraction procedures resulted in a number of fertilized egg isolates. These isolates were called: Sample #19 Top Isolate, Sample #19 Bottom Isolate, Sample #20 Top Isolate, Sample #20 Bottom Isolate, Fraction X Isolate and Sample #2 Isolate. These isolates were then each tested in the radioligand binding assay.

Sample #19 was prepared by weighing out 103 mg of the contents of a Formulation A capsule. Water (10.3 mL) was added and the solution was vortexed for one minute. Thirty mL of ethyl acetate was then added to the solution and the solution was vortexed again for 1 minute. The sample was then centrifuged using a bench top Beckman centrifuge. Three fractions were formed as a result. The top (organic) and bottom (aqueous) fractions were collected separately and the middle fraction was discarded. The top and bottom fractions were each dried down. The bottom (aqueous) fraction was reconstituted in 2.06 mL of water. The sample was not clear and it was centrifuged at 10,000 rpm for ten minutes using a microcentrifuge. The supernatant was removed, labeled as sample 085426-4 (Sample #19 Bottom Isolate) and used in the receptor binding studies. The top (organic) fraction was reconstituted in 1.245 mL of 20% acetonitrile in water. The sample was not clear and it was centrifuged at 10,000 rpm for ten minutes using a microcentrifuge. The supernatant was removed, labeled as sample 085426-3 (Sample #19 Top Isolate) and used in the receptor binding studies. A control for sample #19 was also made. This control consisted of 20% acetonitrile in water, and was labeled as sample 085426-5 in the receptor binding studies.

Sample #20 was prepared by weighing out 249.7 mg of the contents of a Formulation A capsule. Ten mL of 1:1 methanol:dichloromethane was added and the solution was vortexed. Ten mL of dichloromethane was then added to the solution and the solution was vortexed again. The sample was then centrifuged at 3500 rpm for fifteen minutes using a bench-top Beckman centrifuge. Three fractions were formed as a result. The top and bottom organic fractions were collected separately. The middle fraction was discarded. The top and bottom fractions were each dried down and reconstituted in 2.49 mL of 100% methanol in water. The top methanol fraction was semi-clear and the bottom dichloromethane fraction was not soluble. Both samples were centrifuged at 10,000 rpm for ten minutes using a microcentrifuge. The supernatant of each sample was removed. The supernatant from the top methanol fraction was labeled as sample 085426-6 (Sample #20 Top Isolate) and used in the receptor binding studies. The supernatant for the bottom dichloromethane fraction was labeled as sample 085426-7 (Sample #20 Bottom Isolate) and used in the receptor binding studies. A control for sample #20 was also made. This control consisted of 10% methanol in water, and was labeled as sample 085426-9 in the receptor binding studies.

Sample Fraction X was prepared as follows. One hundred twenty-one mg of the contents of a Formulation A capsule was weighed out. Ten mL of water was then added. Ten mL of dichloromethane was then added to the solution and the sample was vortexed. The aqueous and organic fractions were each separately removed. The solvent isolation was repeated by adding 10 mL of dichloromethane to the aqueous fraction and vortexing the solution. Again, the aqueous and organic fractions were each separately removed. The organic fractions from the two isolations were combined and the aqueous fractions from the two isolations were combined. The aqueous and organic fractions were dried down and weighed. The aqueous fraction weighed 116.4 mg and the organic fraction weighed 1.3 mg. The organic fraction was reconstituted in 1.3 mL of 10% methanol in water (for a concentration of 0.1 mg/mL), labeled as sample 085426-8 (Fraction X Isolate) and used in the binding studies. A control for sample Fraction X was also made. This control consisted of 10% methanol in water, and was labeled as sample 085426-9 (note this was the same control as used for sample #20) in the receptor binding studies.

Sample #2 was prepared as follows. A portion (1.8 mg) of the contents of a Formulation A capsule was weighed out. Forty percent PEG in water plus 0.25% Tween 80 (3.6 mL) was then added (for a concentration of 0.5 mg/mL) and the sample was vortexed. This preparation was labeled as sample 085426-1 (Sample #2 Isolate) and was tested in the receptor binding studies. A control for sample #2 was also made. This control consisted of 40% PEG in water plus 0.25% Tween 80, and was labeled as sample 085426-2 in the receptor binding studies.

The results (obtained from duplicate samples of each isolate at maximal concentrations) from the receptor binding study are presented in the following table.

| Target Receptor | #19 Top Isolate | #19 Bottom Isolate | #19 Control | Fraction X Isolate | #20 Top Isolate | #20 Bottom Isolate | #20/ Fraction X Control | #2 Isolate | #2 Control |
|---|---|---|---|---|---|---|---|---|---|
| Glutamate, AMPA | 6% | 95% | 3% | −10% | 97% | 0% | 14% | 38% | −5% |
| Glutamate, Kainate | −9% | 100% | −22% | 1% | 101% | 6% | 2% | 21% | −5% |
| Glutamate, NMDA, Agonist | 2% | 106% | −6% | −10% | 110% | −10% | 0% | 49% | −23% |
| Glutamate, NMDA, glycine | −6% | 63% | 4% | −12% | 92% | −34% | −19% | −18% | −56% |
| Neurokinin 1 | 24% | 9% | 33% | 25% | 21% | −11% | 12% | 87% | 86% |
| Neurokinin 2 | 18% | 13% | 12% | 55% | 53% | 18% | 1% | 102% | 102% |

Bolded data indicate more than 50% inhibition at the concentration tested.

Bolded data indicate more than 50% inhibition at the concentration tested.

Binding by radio-labeled AMPA to the AMPA receptor was inhibited by 97% in the presence of Sample #20 Top Isolate. Binding by radio-labeled kainic acid to the kainate receptor was inhibited by 101% in the presence of Sample #20 Top Isolate. Binding by radio-labeled CGP 39653 to the agonist site of the NMDA receptor was inhibited by 110% in the presence of Sample #20 Top Isolate. Binding by radio-labeled MDL-105,519 to the glycine site that is strychnine-insensitive of the NMDA receptor was inhibited by 92% in the presence of Sample #20 Top Isolate. In addition, the Fraction X Isolate inhibited neurokinin A binding to its NK2 receptor by 55%. To the knowledge of the inventors, this is the first instance in which glutamate receptors and the NK2 receptor have been shown to be antagonized by a single substance.

To further confirm that binding to and activation of the glutamate receptors discussed above and the NK2 receptor are antagonized by Sample #20 Top Isolate, prepared as described above, dose response studies were conducted. Inhibition of binding of the AMPA receptor, the kainate receptor, the agonist site of the NMDA receptor, the glycine (strychnine-insensitive site) of the NMDA receptor and the NK2 receptor were evaluated in the presence of the following concentrations of #20 Top Isolate (based on the amount of Formulation A contained in Sample #20 prior to extraction): 0.1, 0.3, 1.0, 3.0, 10, 30, 100 and 300 μg/mL.

FIG. 8 shows the results of the assay performed with the agonist site (ionotropic) of the NMDA receptor. Sample #20 Top Isolate inhibited the ability of CGP 39653 to bind the agonist site of the NMDA receptor in a concentration-dependent manner, with higher concentrations of Sample #20 Top Isolate providing more binding inhibition and lower concentrations providing less binding inhibition. The $IC_{50}$ of NMDA was determined to be $1.11\times10^{-5}$#g/mL and the $K_i$ was determined to be $9.02\times10^{-6}$ M. The $IC_{50}$ of Sample #20 Top Isolate was determined to be 5.78 μg/mL and the $K_i$ was determined to be 4.69 M.

FIG. 9 shows the results of the assay performed with the kainate receptor. Sample #20 Top Isolate inhibited the ability of glutamate kainic acid to bind the kainate receptor in a concentration-dependent manner, with higher concentrations of Sample #20 Top Isolate providing more binding inhibition and lower concentrations providing less binding inhibition. The $IC_{50}$ of kainic acid was determined to be $1.77\times10^{-8}$ μg/mL and the $K_i$ was determined to be $1.08\times10^{-8}$ M. The $IC_{50}$ of Sample #20 Top Isolate was determined to be 12.0 μg/mL and the $K_i$ was determined to be 7.32 M.

FIG. 10 shows the results of the assay performed with the AMPA receptor. Sample #20 Top Isolate inhibited the ability of AMPA to bind the AMPA receptor in a concentration-dependent manner, with higher concentrations of Sample #20 Top Isolate providing more binding inhibition and lower concentrations providing less binding inhibition. The $IC_{50}$ of (+/−) AMPA HBr was determined to be $3.54\times10^{-8}$ μg/mL and the was determined to be $3.00\times10^{-8}$ M. The $IC_{50}$ of Sample #20 Top Isolate was determined to be 11.7 μg/mL and the K was determined to be 9.91 M.

FIG. 11 shows the results of the assay performed with the glycine (strychnine-insensitive) site of the NMDA receptor. Sample #20 Top Isolate inhibited the ability of MDL-105,519 to bind the glycine (strychnine-insensitive) site of the NMDA receptor in a concentration-dependent manner, with higher concentrations of Sample #20 Top Isolate providing more binding inhibition and lower concentrations providing less binding inhibition. The $IC_{50}$ of MDL-105,519 was determined to be $2.8\times10^{-8}$ μg/mL and the $K_i$ was determined to be $2.36\times10^{-8}$ M. The $IC_{50}$ of Sample #20 Top Isolate was determined to be 21.9 μg/mL and the $K_i$ was determined to be 18.4 M.

FIG. 12 shows the results of the assay performed with the NK2 receptor. Sample #20 Top Isolate inhibited the ability of neurokinin A to bind the NK2 receptor in a concentration-dependent manner, with higher concentrations of Sample #20 Top Isolate providing more binding inhibition and lower concentrations providing less binding inhibition. The $IC_{50}$ of neurokinin A was determined to be $6.84\times10^{-10}$ μg/mL and the $K_i$ was determined to be $5.76\times10^{-10}$ M. The $IC_{50}$ of Sample #20 Top Isolate was determined to be $4.15\times10^{2}$ μg/mL and the $K_i$ was determined to be $3.49\times10^{2}$ M.

REFERENCES

Ahlstedt I, Engberg S, Smith J, Perey C, Moody A, Morten J, Lagerström-Fermér M, Drmota T, von Mentzer B, Påhlman I, Lindström E, Occurrence and pharmacological characterization of four human tachykinin NK2 receptors. Biochenical Pharmacology 2008 76:476-481.

Bai, T, Zhou D, Weir T, Hegele R, Hayashi S, McKay K, Bondy G, Fong T, Substance P (NK1)—and neurokinin A (NK2)—receptor gene expression in inflammatory airway diseases. Am J Physiol Lung Cell Mol Physiol 1995 269:L309-L317.

Beck A T, Ward C H, Mock J, Erbaugh J, An inventory for measuring depression. Archives of General Psychiatry 4:561-571, 1961.

Bowie D, Ionotropic glutamate receptors & CNS disorders. CNS Neural Disord Drug Targets. 2008 April; 7(2):129-43.

Cheon Y, Park J, Joe K H, Kim D J, The effect of 12-week open-label memantine treatment on cognitive function improvement in patients with alcohol-related dementia. Int J Neuropsychopharmacol. 2008 November; 11(7): 971-83. Epub 2008 Mar. 17.

Chez M G, Burton Q, Dowling T, Chang M, Khanna. P, Kramer C J, Memantine as adjunctive therapy in children diagnosed with autistic spectrum disorders: an observation of initial clinical response and maintenance tolerability. Child Neurol. 2007 May; 22(5):574-9.

Chourbaji S, Vogt M A, Funiagalli F, Sohr R, Frasca A, Brandwein C, Hörtnagl H, Riva M A, Sprengel R, Gass P, AMPA receptor subunit 1 (GluR-A) knockout mice model the glutamate hypothesis of depression. FASEB J. 2008 September; 22(9):3129-34. Epub 2008 May 20.

Dableh L J, Yashpal K, Rochford J, Henry J L, Antidepressant-like effects of neurokinin receptor antagonists in the forced swim test in the rat. Eur J Pharmacol. 2005 Jan. 10; 507(1-3):99-105. Epub 2004 Dec. 28.

Davidson J R, Preliminary report: Prevention, control and treatment of human cancer as a deficiency disease. CMAJ 1941; 45:308-312.

Evangelista S, Involvement of tachykinins in intestinal inflammation. Curr Pharm Des. 2001 January; 7(1):19-30.

Ginsberg M D, Neuroprotection for ischemic stroke: past, present and future. Neuropharmacology. 2008 September; 55(3):363-89. Epub 2008 Mar. 4.

Griebel G, Perrault G, Soubrie P, Effects of SR48968, a selective non-peptide NK2 receptor antagonist on emotional processes in rodents. Psychopharmacology (Berl). 2001 November; 158(3):241-251.

Guy W: ECDEU Assessment Manual for Psychopharmacology—Revised (DHEW Publ No ADM 76-338). Rockville, Md., U.S. Department of Health, Education, and Welfare, Public Health Service, Alcohol, Drug Abuse, and Mental Health Administration, NIMH Psychopharmacology Research Branch, Division of Extramural Research Programs, 1976, pp 218-222.

Hamilton, Development of a rating scale for primary depressive illness. Br J Soc Clin Psychiatry 1967; 6:278-279.

Hamilton M, The assessment of anxiety states by rating. Br J Med Psychol 1959; 32:50-55.

Holmes A, Heilig M, Rupniak N M, Steckler T, Griebel G, Neuropeptide systems as novel therapeutic targets for depression and anxiety disorders. Trends Pharmacol Sci. 2003 November; 24(11):580-8.

Husum H, Wortwein G, Andersson W, Bolwig T G, Mathé A A, Gene-environment interaction affects substance P and neurokinin A in the entorhinal cortex and periaqueductal grey in a genetic animal model of depression: implications for the pathophysiology of depression. Int J Neuropsychopharmacol. 2008 February; 11(1):93-101. Epub 2007 May 4.

Hynd M R, Scott H L, Dodd P R, Glutamate-mediated excitotoxicity and neurodegeneration in Alzheimer's disease. Neurochem Int. 2004 October; 45(5):583-95.

Javitt D C, Glutamate as a therapeutic target in psychiatric disorders. Mol Psychiatry. 2004 November; 9(11):984-97, 979.

Kendler K S, Walters E E, Kessler R C, The prediction of length of major depressive episodes: results from an epidemiological sample of female twins. Psychol Med 1997; 27: 107-117.

Kew J N, Kemp J A, Tonotropic and metabotropic glutamate receptor structure and pharmacology. Psychopharmacology (Berl). 2005 April; 179(1):4-29. Epub 2005 Feb. 25.

Koch H J, Uyanik G, Fischer-Barnicol D, Memantine: a therapeutic approach in treating Alzheimer's and vascular dementia. Curr Drug Targets CNS Neurol Disord. 2005 October; 4(5):499-506.

Krystal J H, Sanacora G, Blumberg H, Anand A, Charney D S, Marek G, Epperson C N, Goddard A, Mason G F, Glutamate and GABA systems as targets for novel antidepressant and mood-stabilizing treatments. Mol Psychiatry. 2002; 7 Suppl 1:S71-80.

Lecci A, Capriati A, Maggi C A, Tachykinin NK2 receptor antagonists for the treatment of irritable bowel syndrome. Br J Pharmacol. 2004 April; 141(8):1249-63. Epub 2004 Mar. 22.

Lewis D A, González-Burgos G, Neuropsychopharmacology. Neuroplasticity of neocortical circuits in schizophrenia. 2008 January; 33(1):141-65. Epub 2007 Sep. 5.

Lingjaerde O, Ahlfors U G, Bech P, et al, The UKU Side Effect Rating Scale: a new comprehensive rating scale for psychotrepic drugs, and a cross-sectional study of side effects in neuroleptic-treated patients. Acta Psychiatrica Scandinavica Suppl 76:1-100, 1987.

Louis C, Stemmelin J, Boulay D, Bergis O, Cohen C, Griebel G, Additional evidence for anxiolytic- and antidepressant-like activities of saredutant (SR48968), an antagonist at the neurokinin-2 receptor in various rodent-models. Pharmacol Biochem Behav. 2008 March; 89(1): 36-45. Epub 2007 Nov. 5.

MacDonald A W 3rd, Chafee M V, Translational and developmental perspective on N-methyl-D-aspartate synaptic deficits in schizophrenia. Dev Psychopathol. 2006 Summer; 18(3):853-76.

Maeng S, Zarate C A Jr, The role of glutamate in mood disorders: results from the ketamine in major depression study and the presumed cellular mechanism underlying its antidepressant effects. Curr Psychiatry Rep. 2007 December; 9(6):467-74.

Mathew S J, Manji H K, Charney D S, Novel drugs and therapeutic targets for severe mood disorders. Neuropsychopharmacology. 2008 August; 33(9):2080-92. Epub 2008 Jan. 2.

Mathew S J, Keegan K, Smith L, Glutamate modulators as novel interventions for mood disorders. Rev Bras Psiquiatr. 2005 September; 27(3):243-8. Epub 2005 Oct. 4.

McCullumsmith R E, Clinton S M, Meador-Woodruff J H, Schizophrenia as a disorder of neuroplasticity. Int Rev Neurobiol. 2004; 59:19-45.

McNally L, Bhagwagar Z, Hannestad J, Inflammation, glutamate, and glia in depression: a literature review. CNS Spectr. 2008 June; 13(6):501-10.

McLeod J D, Kessler R C, Landis K R, Recovery from major depressive episodes in a community sample of married men and women. J Abnorm Psychol 1992; 101: 277-286.

Micale V, Tamburella A, Leggio G M, Mazzola C, Li Volsi V, Drago F, Behavioral effects of saredutant, a tachykinin NK2 receptor antagonist, in experimental models of mood disorders under basal and stress-related conditions. Pharmacol Biochem Behav. 2008 September; 90(3):463-9. Epub 2008 Apr. 12.

Miller R G, Mitchell J D, Lyon M, Moore D H, Riluzole for amyotrophic lateral sclerosis (ALS)/motor neuron disease (MND). Cochrane Database Syst Rev. 2007 Jan. 24; (1):CD001447.

Montgomery S A, Asberg M, A new depression scale designed to be sensitive to change. British Journal of Psychiatry 134:382:-389, 1979.

Patten S, The duration of major depressive disorders in the Canadian general population. Chronic Dis Canada 22:1.2001.

Paul I A, Skolnick P, Glutamate and depression: clinical and preclinical studies. Ann N Y Acad Sci. 2003 November; 1003:250-72.

Ravindranath V, Neurolathyrism: mitochondrial dysfunction in excitotoxicity mediated by L-beta-oxalyl aminoalanine. Neurochem Int. 2002 May; 40(6):505-9.

Rizzo C A, Hey J A, Activity of nonpeptide tachykinin antagonists on neurokinin a induced contractions in dog urinary bladder. J Urol. 2000 June; 163(6):1971-4.

Rorick-Kehn L M, Hart J C, McKinzie D L, Pharmacological characterization of stress-induced hyperthermia in DBA/2 mice using metabotropic and ionotropic glutamate receptor ligands. Psychopharmacology (Berl). 2005 December; 1 83(2):226-40. Epub 2005 Nov. 9.

Saloméń, Stemmelin J, Cohen C, Griebel G, Selective blockade of NK2 or NK3 receptors produces anxiolytic- and antidepressant-like effects in gerbils. Pharmacol Biochem Behav. 2006 April; 83(4):533-9. Epub 2006 Apr. 19.

Sanacora G, Rothman D L, Mason G, Krystal J H, Clinical studies implementing glutamate neurotransmission in mood disorders. Ann N Y Acad Sci. 2003 November; 1003:292-308.

Sanacora G, Kendell S F, Levin Y, Simen A A, Fenton L R, Coric V, Krystal J H, Preliminary evidence of riluzole efficacy in antidepressant-treated patients with residual depressive symptoms. Biol Psychiatry. 2007 Mar. 15; 61(6):822-5. Epub 2006 Dec. 4.

Spencer P S, Food toxins, ampa receptors, and motor neuron diseases. Drug Metab Rev. 1999 August; 31(3):561-87.

Steinberg R, Alonso R, Griebel G, Bert L, Jung M, Oury-Donat F, Poncelet M, Gueudet C, Desvignes C, Le Fur G, Soubrié P, Selective blockade of neurokinin-2 receptors produces antidepressant-like effects associated with reduced corticotropin-releasing factor function. J Pharmacol Exp Ther. 2001 November; 299(2):449-58.

Stratton S C, Beresford I J, Harvey F J, Turpin M P, Hagan R M, Tyers M B, Anxiolytic activity of tachykinin NK2 receptor antagonists in the mouse light-dark box. Eur J Pharmacol. 1993 Dec. 21; 250(3):R11-2.

Svenningsson P, Bateup H, Qi H, Takamiya K, Huganir R L, Spedding M, Roth B L, McEwen B S, Greengard P, Involvement of AMPA receptor phosphorylation in antidepressant actions with special reference to tianeptine. Eur J Neurosci. 2007 December; 26(12):3509-17.

Teixeira R M, Santos A R, Ribeiro S J, Calixto J B, Rae G A, De Lima T C, Effects of central administration of tachykinin receptor agonists and antagonists on plus-maze behavior in mice. Eur J Pharmacol. 1996 Sep. 5; 311(1):7-14.

Toro C T, Hallak J E, Dunham J S, Leite J P, Sakamoto A C, Guarnieri R, Fong V, Deakin J F, The NR1 N-methyl-D-aspartate subunit and brain-derived neurotrophic factor in temporal lobe epilepsy hippocampus: a comparison of patients with and without coexisting psychiatric symptoms. Epilepsia. 2007 December; 48(12):2352-6. Epub 2007 Oct. 5.

Toulouse M, Coelho A, Fioramonti J, Lecci A, Maggi C, Bueno L, Role of tachykinin NK2 receptors in normal and altered rectal sensitivity in rats. Br J Pharmacology 2000 129, 193-199.

Treatment of Chronic Depression (Editorial), NEJM 342: 1518-1520, 2000.

Walsh D M, Stratton S C, Harvey F J, Beresford I J, Hagan R M, The anxiolytic-like activity of GR159897, a non-peptide NK2 receptor antagonist, in rodent and primate models of anxiety. Psychopharmacology (Berl). 1995 September; 121(2):186-91.

Walton H S, Dodd P R, Glutamate-glutamine cycling in Alzheimer's disease. Neurochem Int. 2007 June; 50(7-8):1052-66. Epub 2006 Dec. 1.

Ware J E Jr, Sherbourne C D, The MOS 36-item short-form health survey (SF-36). 1. Conceptual framework and item selection Medical Care 1992, 30:473-483.

Zarate C A Jr, Payne J L, Quiroz J, Sporn J, Denicoff K K, Luckenbaugh D, Charney D S, Manji H K, An open-label trial of riluzole in patients with treatment-resistant major depression. Am J Psychiatry. 2004 January; 161(1):171-4.

Zarate C A Jr, Quiroz J A, Singh J B, Denicoff K D, De Jesus G, Luckenbaugh D A, Charney D S, Manji H K, An open-label trial of the glutamate-modulating agent riluzole in combination with lithium for the treatment of bipolar depression. Biol Psychiatry. 2005 Feb. 15; 57(4):430-2.

The invention claimed is:

1. A method for treating a disorder in a patient in need thereof, comprising the step of administering to the patient a therapeutically effective amount of fertilized avian egg isolate comprising freeze-dried embryo, ovalbumin, and clear sac from the fertilized avian egg, said patient having been clinically diagnosed with a disorder selected from the group consisting of anxiety and major depressive mood disorder in accordance with the Diagnostic and Statistical Manual of Mental Disorders-IV-Text Revision (DSM-IV TR) criteria, wherein the therapeutically effective amount ranges from 200 to 4000 mg/day.

2. The method of claim 1, wherein the fertilized avian egg isolate is an aqueous isolate produced by the process comprising the steps of (i) separating the contents of at least one fertilized avian egg from the shell; (ii) combining the contents or retentate in a container; (iii) blending the contents or retentate to produce a slurry, optionally adding a solvent; (iv) mixing the slurry with an aqueous solution for a period of time; (v) centrifuging or filtering the mixture to produce an aqueous solution free of solid material; (vi) separating the aqueous solution from the solid material, (vii) freezing the aqueous solution; and (viii) freeze-drying the aqueous solution to produce the fertilized avian egg isolate.

3. The method of claim 1, wherein the disorder is major depressive mood disorder.

4. The method of claim 1, wherein the disorder is anxiety.

5. The method of claim 2, wherein the fertilized avian egg isolate is an aqueous isolate produced by the process comprising the steps of (i) separating the contents of at least one fertilized avian egg from the shell; (ii) filtering the contents to produce a retentate; (iii) combining the retentate in a container; (iv) blending the retentate to produce a slurry; (v) mixing the slurry with an aqueous solution for a period of time; (vi) centrifuging or filtering the mixture to produce an aqueous solution free of solid material; (vii) separating the aqueous solution from the solid material, (viii) freezing the aqueous solution; and (ix) freeze-drying the aqueous solution to produce the fertilized avian egg isolate.

6. The method of claim 2, wherein the fertilized avian egg isolate is an aqueous isolate produced by the process comprising the steps of (i) separating the contents of at least one fertilized avian egg from the shell; (ii) combining the contents in a container; (iii) blending the contents with a solvent to produce a slurry; (iv) mixing the slurry with an aqueous solution for a period of time; (v) centrifuging or filtering the mixture to produce an aqueous solution free of solid material; (vi) separating the aqueous solution from the solid material, (vii) freezing the aqueous solution; and (viii) freeze-drying the aqueous solution to produce the fertilized avian egg isolate.

7. The method of claim 2, wherein the fertilized avian egg isolate is an aqueous isolate produced by the process comprising the steps of (i) separating the contents of at least one fertilized avian egg from the shell; (ii) filtering the contents to produce a retentate; (iii) combining the retentate in a container; (iv) blending the retentate with a solvent to produce a slurry; (v) mixing the slurry with an aqueous solution for a period of time; (vi) centrifuging or filtering the mixture to produce an aqueous solution free of solid material; (vii) separating the aqueous solution from the solid material, (viii) freezing the aqueous solution; and (ix) freeze-drying the aqueous solution to produce the fertilized avian egg isolate.

8. The method of claim 1, wherein the therapeutically effective amount ranges from 500-3000 mg/day.

9. The method of claim 1, wherein the therapeutically effective amount ranges from 1000-2500 mg/day.

* * * * *